(12) United States Patent
Shen et al.

(10) Patent No.: US 9,901,679 B2
(45) Date of Patent: Feb. 27, 2018

(54) MONITORING CONDITIONS OF AN IMPLANTABLE MEDICAL FLUID DELIVERY DEVICE

(71) Applicant: Medtronic, Inc., Minneapolis, MN (US)

(72) Inventors: Jiaying Shen, Maple Grove, MN (US); Emem D. Akpan, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 354 days.

(21) Appl. No.: 14/677,436

(22) Filed: Apr. 2, 2015

(65) Prior Publication Data
US 2015/0209513 A1    Jul. 30, 2015

Related U.S. Application Data

(62) Division of application No. 12/961,874, filed on Dec. 7, 2010, now Pat. No. 8,998,841.

(Continued)

(51) Int. Cl.
*A61M 31/00* (2006.01)
*A61M 5/172* (2006.01)
(Continued)

(52) U.S. Cl.
CPC ...... *A61M 5/1723* (2013.01); *A61M 5/14276* (2013.01); *A61M 5/16859* (2013.01);
(Continued)

(58) Field of Classification Search
CPC .......... A61M 5/14276; A61M 5/16859; A61M 5/16854; G06F 19/3412; G06F 19/3468
See application file for complete search history.

(56) References Cited

U.S. PATENT DOCUMENTS

| | | |
|---|---|---|
| 4,551,133 A | 11/1985 | Zegers de Beyl et al. |
| 5,609,576 A | 3/1997 | Voss et al. |

(Continued)

FOREIGN PATENT DOCUMENTS

| | | |
|---|---|---|
| WO | 02064040 A2 | 8/2002 |
| WO | 05089860 A1 | 9/2005 |
| WO | 07123764 A2 | 11/2007 |

OTHER PUBLICATIONS

Communication pursuant to Rules 161(1) and 162 EPC from counterpart European patent application No. 10795865.4, dated Aug. 17, 2012, 2 pp.

(Continued)

*Primary Examiner* — Aarti B Berdichevsky
(74) *Attorney, Agent, or Firm* — Shumaker & Sieffert, P.A.

(57) ABSTRACT

A programmer device includes an interface that communicates with an implantable fluid delivery device and a user interface that allows a user to troubleshoot a catheter connected to the fluid delivery device by measuring a pressure associated with the catheter. A processor may compare the measured pressure waveform to a previously-acquired waveform or the user interface may display the measured pressure waveform for the user to compare the displayed pressure waveform to a previously-acquired baseline waveform. The comparison between the two waveforms may be based on the pressure decay time. A historical log of measured pressure decays associated with the catheter may be maintained by the programmer device or the implantable fluid delivery device and displayed for the user to determine whether the performance of the catheter is deteriorating.

20 Claims, 36 Drawing Sheets

Related U.S. Application Data

(60) Provisional application No. 61/285,876, filed on Dec. 11, 2009.

(51) Int. Cl.
*A61M 5/142* (2006.01)
*A61M 5/168* (2006.01)
*G06F 19/00* (2018.01)
*A61M 25/04* (2006.01)
*A61M 25/00* (2006.01)

(52) U.S. Cl.
CPC ......... *A61M 25/04* (2013.01); *G06F 19/3412* (2013.01); *G06F 19/3468* (2013.01); *A61M 2025/0002* (2013.01); *A61M 2205/3355* (2013.01); *A61M 2205/50* (2013.01); *A61M 2205/502* (2013.01); *A61M 2205/52* (2013.01)

(56) References Cited

U.S. PATENT DOCUMENTS

| | | | |
|---|---|---|---|
| 5,800,387 | A | 9/1998 | Duffy et al. |
| 5,906,589 | A | 5/1999 | Gordon et al. |
| 6,562,001 | B2 | 5/2003 | Lebel et al. |
| 6,620,151 | B2 | 9/2003 | Blischak et al. |
| 6,945,954 | B2 | 9/2005 | Hochman et al. |
| 7,320,676 | B2 | 1/2008 | Miesel |
| 7,437,644 | B2 | 10/2008 | Ginggen et al. |
| 7,452,190 | B2 | 11/2008 | Bouton et al. |
| 7,462,163 | B2 | 12/2008 | Yap et al. |
| 7,867,192 | B2 | 1/2011 | Bowman et al. |
| 8,162,888 | B2 | 4/2012 | Kalpin |
| 8,167,832 | B2 | 5/2012 | Bowman et al. |
| 8,317,770 | B2 | 11/2012 | Miesel et al. |
| 8,323,268 | B2 | 12/2012 | Ring et al. |
| 8,352,043 | B2 * | 1/2013 | Goetz ............... A61M 5/14276 607/60 |
| 8,612,055 | B2 * | 12/2013 | Ali ................... A61M 5/16831 604/19 |
| 8,998,841 | B2 * | 4/2015 | Shen ................. A61M 5/14276 604/67 |
| 2003/0065308 | A1 | 4/2003 | Lebel et al. |
| 2005/0075624 | A1 | 4/2005 | Miesel |
| 2006/0079862 | A1 | 4/2006 | Genosar |
| 2006/0276744 | A1 | 12/2006 | Falk |
| 2007/0270782 | A1 | 11/2007 | Miesel et al. |
| 2008/0125702 | A1 | 5/2008 | Blischak et al. |
| 2008/0139996 | A1 | 6/2008 | Bowman et al. |
| 2010/0010581 | A1 * | 1/2010 | Goetz ............... A61M 5/14276 607/60 |
| 2010/0010646 | A1 * | 1/2010 | Drew ................. A61M 5/14276 700/86 |
| 2010/0145300 | A1 | 6/2010 | Shelton et al. |
| 2010/0185182 | A1 * | 7/2010 | Alme ................. A61M 5/14276 604/891.1 |
| 2010/0185183 | A1 * | 7/2010 | Alme ................. A61M 5/14276 604/891.1 |
| 2010/0280446 | A1 | 11/2010 | Kalpin |
| 2011/0257798 | A1 * | 10/2011 | Ali ..................... A61M 5/16831 700/282 |
| 2011/0264034 | A1 * | 10/2011 | Roberts ............... G06F 19/3418 604/65 |
| 2012/0265033 | A1 * | 10/2012 | Akpan ................ A61M 5/1723 600/309 |

OTHER PUBLICATIONS

Response to Communication pursuant to Rules 161(1) and 162 EPC from counterpart European patent application No. 10795865.4, dated Feb. 25, 2013, 4 pp.

International Search Report and the Written Opinion from counterpart International Application No. PCT/US2010/059788, dated Feb. 2, 2011, 10 pp.

International Preliminary Report on Patentability from counterpart International Application No. PCT/US2010/059788, dated Jun. 12, 2012, 6 pp.

Prosecution History from U.S. Appl. No. 12/961,874, dated from Jul. 18, 2013 through Nov. 26, 2014, 67 pp.

* cited by examiner

MONITORING CONDITIONS OF AN IMPLANTABLE MEDICAL FLUID DELIVERY DEVICE

This application is a divisional of U.S. patent application Ser. No. 12/961,874, entitled "MONITORING CONDITIONS OF IMPLANTABLE MEDICAL FLUID DELIVERY DEVICE" and filed Dec. 7, 2010, which claims the benefit of U.S. Provisional Patent Application No. 61/285,876, entitled "MONITORING CONDITIONS OF IMPLANTABLE MEDICAL FLUID DELIVERY DEVICE" and filed on Dec. 11, 2009, the entire contents of both of which are incorporated herein by reference.

TECHNICAL FIELD

This disclosure relates generally to implantable medical devices and, more particularly, to implantable medical fluid delivery systems.

BACKGROUND

Medical devices, such as implantable therapy delivery devices, may be used in different therapeutic applications, such as chronic delivery of therapy to patients suffering from a variety of conditions, such as pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Pumps or other fluid delivery devices may be used for chronic delivery of therapeutic agents, such as drugs, to address some of the above conditions or disorders. Typically, such devices provide therapy continuously or periodically according to parameters specified by a therapy program. A therapy program may comprise respective values, specified by a clinician, for each of a plurality of parameters.

One type of implantable fluid delivery device is a drug infusion device that can deliver a fluid medication to a patient at a selected site in the patient's body. A drug infusion device may be implanted at a location in the body of a patient and deliver a fluid medication through a catheter to a selected delivery site in the body. Drug infusion devices, such as implantable drug pumps, include fluid reservoirs that may be self-sealing and may be accessible through ports. A drug infusion device may be configured to deliver a therapeutic agent from the fluid reservoir to a patient according to a therapy program, which may, for example, specify a rate of delivery by the implantable device of a fluid delivered to the patient.

Programmable implantable medical devices (IMDs) are typically programmed using an external programming device, sometimes known as a controller or programmer, which can communicate with the IMD through well-known techniques, such as telemetry, to download a therapy program. An external controller or programmer can be used by a medical professional, for example, to change the therapeutic regimen by increasing or decreasing the amount of fluid medication delivered, or by increasing or decreasing the intensity or timing or characteristic of an electrical stimulation signal. Typically, a medical professional interfaces with the external controller or programmer to set various parameters associated with the IMD and then transmits, or downloads, those parameters, e.g., a therapy program, to the IMD. The external controller or programmer may also record other information important to the delivery of the therapy. Some information may be stored in the IMD and/or the external controller or programmer. Such information may include, for example, patient information or IMD information. IMD information may include, as examples, the model of the IMD, volume of fluid the IMD is capable of containing, implant location, length of catheter or lead, and other information specific to different devices.

SUMMARY

In general, the disclosure is directed to monitoring the condition and performance of an implantable medical device. Particularly, the techniques of this disclosure are described in terms of an implantable medical fluid delivery device, which may be implanted in a body of a patient to deliver doses of drug through a catheter. The techniques of this disclosure may be used to determine characteristics of the catheter, and for troubleshooting the catheter. The techniques may measure a pressure associated with pumping fluid doses through the catheter, and establish a baseline pressure decay profile for a pump stroke of the implantable device to determine catheter patency.

In one example, the disclosure is directed to an implantable fluid delivery system comprising a catheter, a fluid delivery pump coupled to the catheter, and configured to deliver a fluid through the catheter to a patient, at least one pressure sensor arranged to measure a pressure associated with the catheter during delivery of the fluid to the patient, and a processor configured to define a current pressure waveform based on the measured pressure, wherein the processor is configured to at least one of: determine a characteristic of the catheter based on a comparison of at least a portion of the current pressure waveform to at least a portion of a previously-acquired pressure waveform, or display, on a display device, at least a portion of the current pressure waveform and at least a portion of a previously-acquired pressure waveform, for a user to determine a characteristic of the catheter based on a comparison of at least a portion of the current pressure waveform to at least a portion of a previously-acquired pressure waveform.

In another example, the disclosure is directed to a method of troubleshooting an implantable catheter associated with an implantable medical fluid delivery device, the method comprising delivering a fluid from the implantable medical fluid delivery device through the catheter to a patient, measuring a pressure associated with the catheter during the delivery of the fluid to the patient, defining a current pressure waveform based on the measured pressure, and at least one of: determining a characteristic of the catheter based on a comparison of at least a portion of the current pressure waveform to at least a portion of a previously-acquired pressure waveform, or displaying, on a display device, at least a portion of the current pressure waveform and at least a portion of a previously-acquired pressure waveform, for a user to determine a characteristic of the catheter based on a comparison of at least a portion of the current pressure waveform to at least a portion of a previously-acquired pressure waveform.

In another example, the disclosure is directed to a computer-readable medium comprising instructions for causing a programmable processor in an implantable fluid delivery system to deliver a fluid from the implantable medical fluid delivery device through a catheter to a patient, measure a pressure associated with the catheter during the delivery of the fluid to the patient, define a current pressure waveform based on the measured pressure, and at least one of: determine a characteristic of the catheter based on a comparison of at least a portion of the current pressure waveform to at least a portion of a previously-acquired pressure waveform, or display, on a display device, at least a portion of the current pressure waveform and at least a portion of a previously-acquired pressure waveform, for a user to determine a characteristic of the catheter based on a comparison of at least a portion of the current pressure waveform to at least a portion of a previously-acquired pressure waveform.

In another example, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable storage medium may be a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

In another example, the disclosure is directed to a system comprising means for delivering a fluid from a implantable medical fluid delivery device through a catheter to a patient, means for measuring a pressure associated with the catheter during the delivery of the fluid to the patient, means for defining a current pressure waveform based on the measured pressure, and at least one of: means for determining a characteristic of the catheter based on a comparison of at least a portion of the current pressure waveform to at least a portion of a previously-acquired pressure waveform, or means for displaying, on a display device, at least a portion of the current pressure waveform and at least a portion of a previously-acquired pressure waveform, for a user to determine a characteristic of the catheter based on a comparison of at least a portion of the current pressure waveform to at least a portion of a previously-acquired pressure waveform.

The details of one or more examples of the disclosure are set forth in the accompanying drawings and the description below. Other features, objects, and advantages will be apparent from the description and drawings, and from the claims.

DETAILED DESCRIPTION

Figure 1:
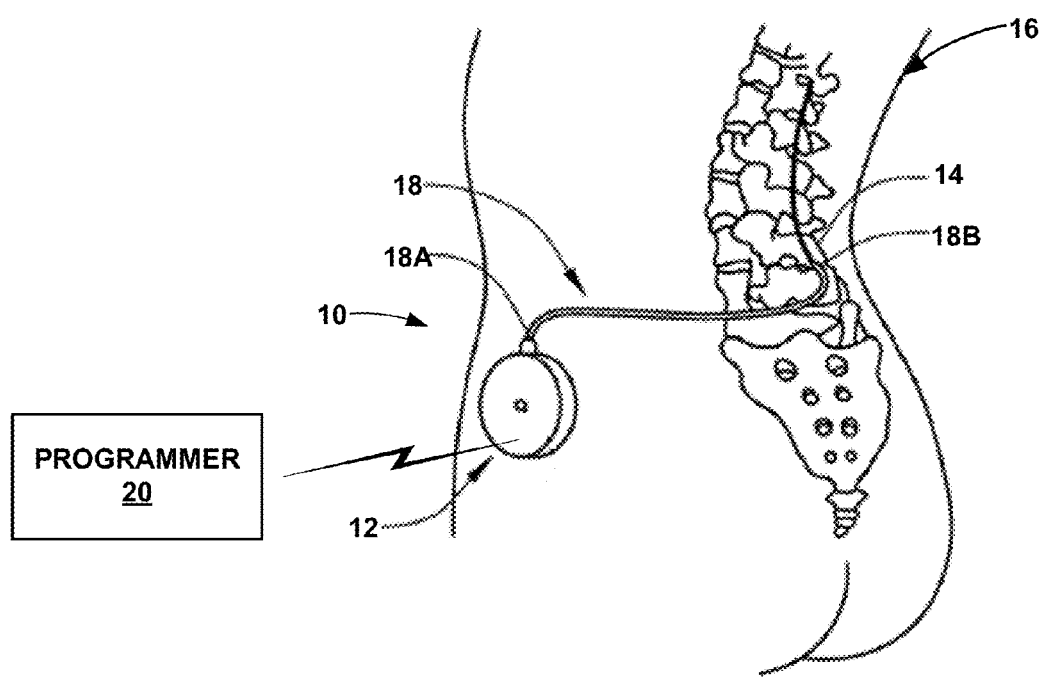
FIG. 1 is a conceptual diagram illustrating an example of a fluid delivery system, which includes an implantable medical device that is configured to deliver a therapeutic agent to a patient via a catheter.

Medical devices are useful for treating, managing, or otherwise controlling various patient conditions or disorders including, for example, pain (e.g., chronic pain, post-operative pain, or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Some medical devices, referred to herein generally as fluid delivery devices, may be configured to deliver one or more fluid therapeutic agents, alone or in combination with other therapies, such as electrical stimulation, to one or more target sites within a patient's body. For example, in some cases, a fluid delivery device may deliver pain-relieving drug(s) to patients with chronic pain, insulin to a patient with diabetes, or other fluids to patients with different disorders. The device may be implanted in the patient for chronic therapy delivery (i.e., therapy lasting longer than a temporary, trial basis) or temporary therapy delivery.

As used in this disclosure, the terms dosing program or therapy program generally refer to a program sent to an implantable fluid delivery device by a programming device to cause the fluid delivery device to deliver fluid at a certain rate and at certain times or time intervals. The dosing program may include, for example, definitions of a priming bolus, a bridging bolus, a supplemental bolus, and a therapy schedule. A dosing program may include additional information, such as patient information, permissions for a user to add a supplemental bolus, historical therapy schedules, fluid or drug information, or other information.

The term therapy schedule may generally refer to a rate (which may be zero or more) at which to administer a fluid, a drug, or a drug combination within the fluid, at specific times to a patient. In particular, the therapy schedule may define one or more programmed doses, which may be periodic or aperiodic, each dose including, for example, a rate of fluid delivery and a time duration or time intervals at which to deliver the dose. Dose generally refers to the amount of drug delivered over a period of time (e.g., milligrams per day), and may change over the course of a therapy schedule such that a drug may be delivered at different rates at different times. In other examples, the amount and frequency of delivery of drug may vary according to the amount of activity or a posture of the user (e.g., sitting, walking, lying down, or the like).

In accordance with various techniques described in this disclosure, a programmer device that programs an implantable fluid delivery device may display programming tasks via a user interface, where at least one of the tasks allows a user to troubleshoot the catheter and/or pump to ensure proper and safe delivery of the therapeutic agent (e.g., drug)

to the patient. Troubleshooting the catheter and/or pump may comprise, for example, determining a patency associated with the catheter. The determined patency of the catheter may allow a user to determine, for example, whether there is blockage or interruption of fluid flow through the catheter or whether the catheter is functioning properly. The fluid flow through the catheter may be affected by such factors as, for example, tissue build-up, or bending or displacement of the catheter. Once the patency of the catheter falls below a certain level, the programmer may indicate an alert automatically, or a user may make a determination based on information displayed on the user interface of the programmer, and the catheter may be revised, repaired, or replaced.

In one example, a user may utilize the programmer to initiate a measurement of a pressure associated with pumping fluid doses through the catheter. The pressure associated with the catheter may be a pressure in the catheter, or in any element in communication (e.g., fluid communication) with the catheter, such as any conduit in communication with the catheter and/or the pump through which the pump delivers a therapeutic agent, e.g., tubing in the fluid delivery device. The measured pressure may be used to establish a baseline pressure decay profile for a pump stroke of the implantable device to determine catheter patency. The baseline pressure decay profile may be a waveform, defined based on the measured pressure, and may provide information such as the decay time associated with a pump stroke, as well as other information such as, for example, information regarding heart beat and respiration. A user may determine when the catheter and pump are functioning properly and measure a baseline pressure decay profile during that time. The baseline pressure decay profile measured during proper functioning of a catheter and pump may be used for comparison to subsequent pressure measurements. The baseline pressure decay profile, for brevity, may be referred to in this disclosure as a baseline or baseline measurement or pressure.

Over time, the baseline measurement may be updated. A history of baseline measurements may be used to predict pump lifetime. Historical baseline measurements may be saved in the system to determine change of catheter and pump behavior over time. Additionally, baseline measurements may be obtained at different postures, as catheter and pump characteristics may be affected by patient's posture (e.g., sitting, walking, sleeping, and the like).

In one example, the programmer may alert a user if no baseline is stored for a patient associated with the connected fluid delivery device. In another example, the programmer may automatically update the baseline by obtaining a new baseline pressure decay profile and replacing the current baseline. In other examples, the baseline may be obtained while the patient is in different postures, and the baseline for each posture may be stored to perform a comparison of subsequent pressure measurements at different postures. In another example, the programmer may automatically obtain a new baseline pressure decay profile, and may automatically detect the posture of the patient to store the new baseline for the corresponding posture.

In one example, a user may indicate a need for a baseline or an updated baseline by requesting a pump stroke, and the programmer may obtain a baseline when the next scheduled dose is delivered to the patient. In another example, the user may not want to wait until the next dose is delivered and may request a dose to be delivered sooner than the next scheduled dose for the purpose of determining a baseline for a pump stroke. In another example, the programmer may obtain and store baselines associated with certain catheter and pump malfunctions and/or conditions, such as catheter occlusion or disconnection. Certain catheter malfunctions and/or conditions may be detected using, for example, techniques such as those disclosed in U.S. patent application Ser. No. 11/731, 355, entitled "SYSTEMS AND METHODS OF IDENTIFYING CATHETER MALFUNCTIONS USING PRESSURE SENSING," filed on Mar. 30, 2007, the entire contents of which being incorporated herein by reference.

Techniques described in this disclosure may incorporate the use of therapy systems with one or more pressure sensors configured to measure pressure somewhere within the fluid pathway of an implantable fluid delivery device, such as a catheter extending from the device and/or internal tubing within the device. Such techniques may be performed when the catheter is implanted or outside the body prior to implantation. In some cases, pressure may be measured while a dose of the therapeutic agent, or a portion of a dose, is delivered to the patient. In some cases, the pressure may be measured in response to a single stroke of a pump that delivers the fluid to the catheter. Other measurements that may be incorporated into techniques described in this disclosure may be, for example, catheter length measurements. Example techniques for determining catheter length are disclosed in U.S. patent application Ser. No. 12/433,836, entitled "AUTOMATED CATHETER LENGTH DETERMINATION FOR IMPLANTABLE FLUID DELIVERY DEVICE," filed on Apr. 30, 2009, the entire content of which being incorporated herein by reference.

FIG. 1 is a conceptual diagram illustrating an example of a therapy system 10, which includes implantable medical device (IMD) 12, catheter 18, and external programmer 20. IMD 12 is connected to catheter 18 to deliver at least one therapeutic agent, such as a pharmaceutical agent, pain relieving agent, anti-inflammatory agent, gene therapy agent, or the like, to a target site within patient 16. Example therapeutic agents that IMD 12 can be configured to deliver include, but are not limited to, insulin, morphine, hydromorphone, bupivacaine, clonidine, other analgesics, genetic agents, antibiotics, nutritional fluids, hormones or hormonal drugs, gene therapy drugs, anticoagulants, cardiovascular medications or chemotherapeutics.

In the example of FIG. 1, the therapeutic agent is a therapeutic fluid, which IMD 12 delivers to patient 16 through catheter 18 from proximal end 18A coupled to IMD 12 to distal end 18B located proximate to the target site. Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

Programmer 20 may include a user interface that may display a representation of a portion of an implantable fluid delivery device and simultaneously display an indication of a location of fluid within the implantable fluid delivery device. In one example, the user interface may display a menu from which the user may select a programming task such as, for example, refill the pump and/or adjust pump settings, implant/replace the pump, revise the catheter, or troubleshoot the catheter/pump. In one example, troubleshooting may be selected to determine such issues as patency of the catheter, as will be described below in more detail.

IMD 12, in general, may have an outer housing that is constructed of a biocompatible material (e.g., titanium or biologically inert polymers) that resists corrosion and degradation from bodily fluids. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent. In still other examples, IMD 12 may be external to patient 16 with a percutaneous catheter connected between IMD 12 and the target delivery site within patient 16.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spine 14. Catheter 18 is positioned such that one or more fluid delivery outlets (not shown in FIG. 1) of catheter 18 are proximate to the one or more targets within patient 16. In the example of FIG. 1, IMD 12 delivers a therapeutic agent through catheter 18 to one or more targets proximate to spinal cord 14. IMD 12 can be configured for intrathecal drug delivery into the intrathecal space or epidural delivery into the epidural space, both of which surround spinal cord 14. The epidural space (also known as "extradural space" or "peridural space") is the space within the spinal canal (formed by the surrounding vertebrae) lying outside the dura mater, which encloses the arachnoid mater, subarachnoid space, the cerebrospinal fluid, and spinal cord 14. The intrathecal space is within the subarachnoid space, which is past the epidural space and dura mater and through the theca.

Although the target site shown in FIG. 1 is proximate to spinal cord 14 of patient 16, other applications of therapy system 10 include alternative target delivery sites. The target delivery site in other applications of therapy system 10 can be located within patient 16 proximate to, e.g., sacral nerves (e.g., the S2, S3, or S4 sacral nerves) or any other suitable nerve, organ, muscle or muscle group in patient 16, which may be selected based on, for example, a patient condition. In one such application, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve. Positioning catheter 18 to deliver a therapeutic agent to various sites within patient 16 enables therapy system 10 to assist in managing, for example, peripheral neuropathy or post-operative pain mitigation, ilioinguinal nerve therapy, intercostal nerve therapy, gastric stimulation for the treatment of gastric motility disorders and/or obesity, and muscle stimulation, or for mitigation of other peripheral and localized pain (e.g., leg pain or back pain). As another example, catheter 18 may be positioned to deliver a therapeutic agent to a deep brain site or within the heart (e.g., intraventricular delivery of the agent). Delivery of a therapeutic agent within the brain may help manage any number of disorders or diseases including, for example, depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

As mentioned above, therapy system 10 may be used to reduce pain experienced by patient 16. In such an application, IMD 12 may deliver one or more therapeutic agents to patient 16 according to one or more dosing programs that set forth different therapy parameters, such as a therapy schedule specifying programmed doses, dose rates for the programmed doses, and specific times to deliver the programmed doses. The dosing programs may be a part of a program group for therapy, where the group includes a plurality of dosing programs and/or therapy schedules. In some examples, IMD 12 may be configured to deliver a therapeutic agent to patient 16 according to different therapy schedules on a selective basis. IMD 12 may include a memory to store one or more therapy programs, instructions defining the extent to which patient 16 may adjust therapy parameters, switch between dosing programs, or undertake other therapy adjustments. Patient 16 or a clinician may select and/or generate additional dosing programs for use by IMD 12 via external programmer 20 at any time during therapy or as designated by the clinician.

In some examples, multiple catheters 18 may be coupled to IMD 12 to target the same or different tissue or nerve sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1, though it should be understood that this discussion is applicable to systems with multiple catheters that may have multiple targets and/or deliver multiple therapeutic agents.

Programmer 20 is an external computing device that is configured to communicate with IMD 12 by wireless telemetry. For example, programmer 20 may be a clinician programmer that the clinician uses to communicate with IMD 12. Alternatively, programmer 20 may be a patient programmer that allows patient 16 to view and modify therapy parameters to a limited extent as defined by a clinician or physician. The clinician programmer may include additional or alternative programming features different from those available on the patient programmer. For example, more complex or sensitive tasks may only be allowed by the clinician programmer to prevent patient 16 from making undesired or unsafe changes to the operation of IMD 12, or limitations on the rate of delivery of doses of therapeutic agents (e.g., milligrams per hour or day) may be set in the patient programmer to prevent overdosing.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or his/her fingers to provide input to the display.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured with an application to simulate programmer 20. Alternatively, a notebook computer, tablet computer, or other personal computer may enter an application to become programmer 20 with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 18, the position of catheter 18 within patient 16, the length of catheter 18 at implantation as measured by the implanting physician and/or as automatically estimated by IMD 12, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

The clinician uses programmer 20 to program IMD 12 with one or more therapy programs that define the therapy delivered by the IMD. During a programming session, the clinician may determine one or more dosing programs that may provide effective therapy to patient 16. Patient 16 may provide feedback to the clinician as to efficacy of a program being evaluated or desired modifications to the program. Once the clinician has identified one or more programs that may be beneficial to patient 16, the patient may continue the evaluation process and determine which dosing program or therapy schedule best alleviates the condition of the patient or otherwise provides efficacious therapy to the patient.

The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental boluses such as patient-initiated boluses (e.g., a lock-out interval), a maximum dose that may be delivered over a given time interval, and so forth. IMD 12 may include a feature that prevents dosing the therapeutic agent in a manner inconsistent with the dosing program. Programmer 20 may assist the clinician in the creation/identification of dosing programs by providing a methodical system of identifying potentially beneficial therapy parameters.

A dosage of a therapeutic agent, such as a drug, may be expressed as an amount of drug, e.g., measured in milligrams or other volumetric units, provided to patient 16 over a time interval, e.g., per day or twenty-four hour period. In this sense, the dosage may indicate a rate of delivery. This dosage amount may convey to the caregiver an indication of the probable efficacy of the drug and the possibility of side effects. In general, a sufficient amount of the drug should be administered in order to have a desired therapeutic effect, such as pain relief. However, the amount of the drug administered to the patient should be limited to a maximum amount, such as a maximum daily dose, in order not to avoid potential side effects or overdosing. Program information specified by a user via programmer 20 may be used to control dosage amount, dosage rate, dosage time, maximum dose for a given time interval (e.g., daily), or other parameters associated with delivery of a drug or other fluid by IMD 12.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 needs to be replaced or recharged.

Whether programmer 20 is configured for clinician or patient use, programmer 20 may communicate to IMD 12 or any other computing device via wireless communication. Programmer 20, for example, may communicate via wireless communication with IMD 12 using radio frequency (RF) telemetry techniques known in the art or other standard communication protocols such as, for example, Bluetooth®. Programmer 20 may also communicate with another programmer or computing device via a wired or wireless connection using any of a variety of communication techniques including, e.g., RF communication according to the 802.11 or Bluetooth® specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks including, e.g., non-volatile memory. Further, programmer 20 may communicate with IMD 12 and another programmer via, e.g., a local area network (LAN), wide area network (WAN), public switched telephone network (PSTN), or cellular telephone network, or any other terrestrial or satellite network appropriate for use with programmer 20 and IMD 12.

In accordance with catheter patency determination techniques described in detail below, therapy system 10 of FIG. 1 may include one or more pressure sensors that are configured to measure a pressure pulse within catheter 18 during the delivery of a fluid dose. The fluid dose may be an actual fluid dose delivered within patient 16, a test dose delivered outside the patient, or a test dose of a test fluid delivered within the patient. IMD 12 includes control electronics, e.g. one or more processors and non-volatile memories that are configured to receive the measured pressure pulse within catheter 18 from the pressure sensor(s). The processor may utilize the measured pressure pulse to make determinations regarding the catheter patency, directly from the pressure pulse measurement or by using the measured pressure pulse to determine other factors (e.g., calculating an estimated length of catheter 18).

Measuring the pressure pulse within catheter 18 can include determining a maximum pressure within the catheter and determining a decay time of the pressure pulse. The decay time of a pressure pulse, generally speaking, is the time required for the pressure pulse within the catheter to fall from a maximum pressure level to a signature pressure level. The maximum pressure level may be a pressure sensed upon delivery of a pump stroke, e.g., pumping a drug dosage through the catheter. The signature pressure level may be the pressure in the catheter during non-therapy time, i.e., when a pump stroke or its effects are not present. When there are no pump stroke effects, the catheter may be filled with CSF, for example, and the pressure of the catheter filled with only CSF may be the signature pressure level. The signature pressure level may be somewhat constant, and may have slight variations based on other body functions. In one example, catheter problems may be detectable from variations in the signature pressure level exceeding a normal amount. IMD 12 can be configured to measure a signature pressure level within the catheter at the time of implantation.

Determining the patency of the catheter may include, e.g., establishing a baseline pressure decay profile for a pump stroke of the implantable infusion system, and determining catheter patency based on the established baseline pressure decay. The catheter patency determination may be initiated automatically, e.g., by IMD 12 or programmer 20, avoiding the need for human intervention. In some cases, the catheter patency determination may be initiated at the request of a user, e.g., manually by a human caregiver or user of the programmer 20 such as, for example, a doctor or clinician. Pressure measurement to determine catheter patency may be performed when the catheter is implanted in the patient and the pump is implanted in the patient (in vivo) or when the pump is outside the patient prior to pump implantation (ex vivo).

The baseline pressure decay may be measured at intervals specified by the user at the time of implantation or at a subsequent time using the programmer 20. The time intervals may be determined based on how long a catheter had been implanted in the patient, or may be specified by a user. In one example, the baseline pressure decay may be measured at a random time determined by a user. In another example, an alert may be displayed by the programmer 20 indicating to a user to initiate a determination of baseline pressure decay profile when a pump stroke is delivered. In an example, a log of historical measurements of baseline pressure decay may be maintained in the IMD 12 and/or the programmer 20, or in a storage device accessible by the user, to which the IMD 12 and/or the programmer 20 may connect to retrieve historical measurements for a patient.

Additionally, IMD 12 and/or the programmer 20 may be configured to analyze the measured baseline pressure decay to troubleshoot the catheter. In some cases, catheter 18 may become disconnected from IMD 12 or otherwise malfunction due to, as examples, cuts or occlusions in the catheter or blockage at the open end of the catheter 18, e.g., due to tissue build up or shifting. In an example, IMD 12 may determine if the decay time is below a minimum threshold value, which may indicate a leak in catheter 18. In another example, IMD 12 may determine if the decay time is above a maximum threshold value, which may indicate an occlusion in catheter 18. IMD 12 may also analyze the pressure pulse by determining if the pressure within the lumen falls below the signature pressure level after decaying from a maximum pressure, which may indicate either a cut in catheter 18 or that catheter 18 is disconnected from IMD 12. The signature pressure level may be the pressure level in the catheter 18 when no drug is pumped through the catheter, i.e., before a pump stroke is delivered and after the pressure has decayed following a pump stroke delivery. In one example, the pressure associated with the catheter may be determined based on the duration of the portion where the pressure is above a baseline pressure level (e.g., the signature pressure level). The portion where the pressure is above the baseline pressure level may be the portion corresponding to the initial rise in the pressure in response to the pump stroke delivery and until the pressure level decays back to the signature pressure level.

In general, the determination of the baseline pressure decay profile may be presented to a user such as, for example, a clinician via a user interface of programmer 20. The clinician may then determine a catheter patency issue based on the determined baseline and an appropriate course of action such as, for example, replacing or adjusting the catheter and/or pump. In some cases, the determined baseline may be used as an optimal baseline to which subsequent pressure measurements may be compared to determine whether there may be a deviation from the baseline pressure indicating a malfunction in the catheter and/or pump. In other case, the determined baseline may be compared to a previously determined baseline and/or an optimal baseline to determine the degree of deterioration in the performance of the catheter and/or pump. The optimal baseline may be, for example, a baseline determined when the pump and catheter are performing reasonably well or at the time of implantation. In some examples, baselines may be posture-dependent and a baseline obtained at a certain posture may be compared to an optimal baseline associated with the same posture.

If the determined baseline is perceived to be faulty by a clinician, or inconsistent with an expected behavior, the clinician may be able to request a pump stroke to make another determination, i.e., to obtain a new baseline pressure decay profile measurement. The new baseline pressure decay profile may then be used for comparison with subsequent pressure measurements to evaluate catheter patency. The clinician's ability to request a pump stroke to obtain a pressure measurement may depend on several factors such as, for example, the dosage in each delivered stroke, the time elapsed since the last stroke, and the therapy program for the patient, among other factors. The determined baselines may be logged to show historical trends in the performance of the catheter and/or pump. In some cases, the determined baselines may be categorized based on the position of the patient at the time a baseline is obtained.

Figure 2:
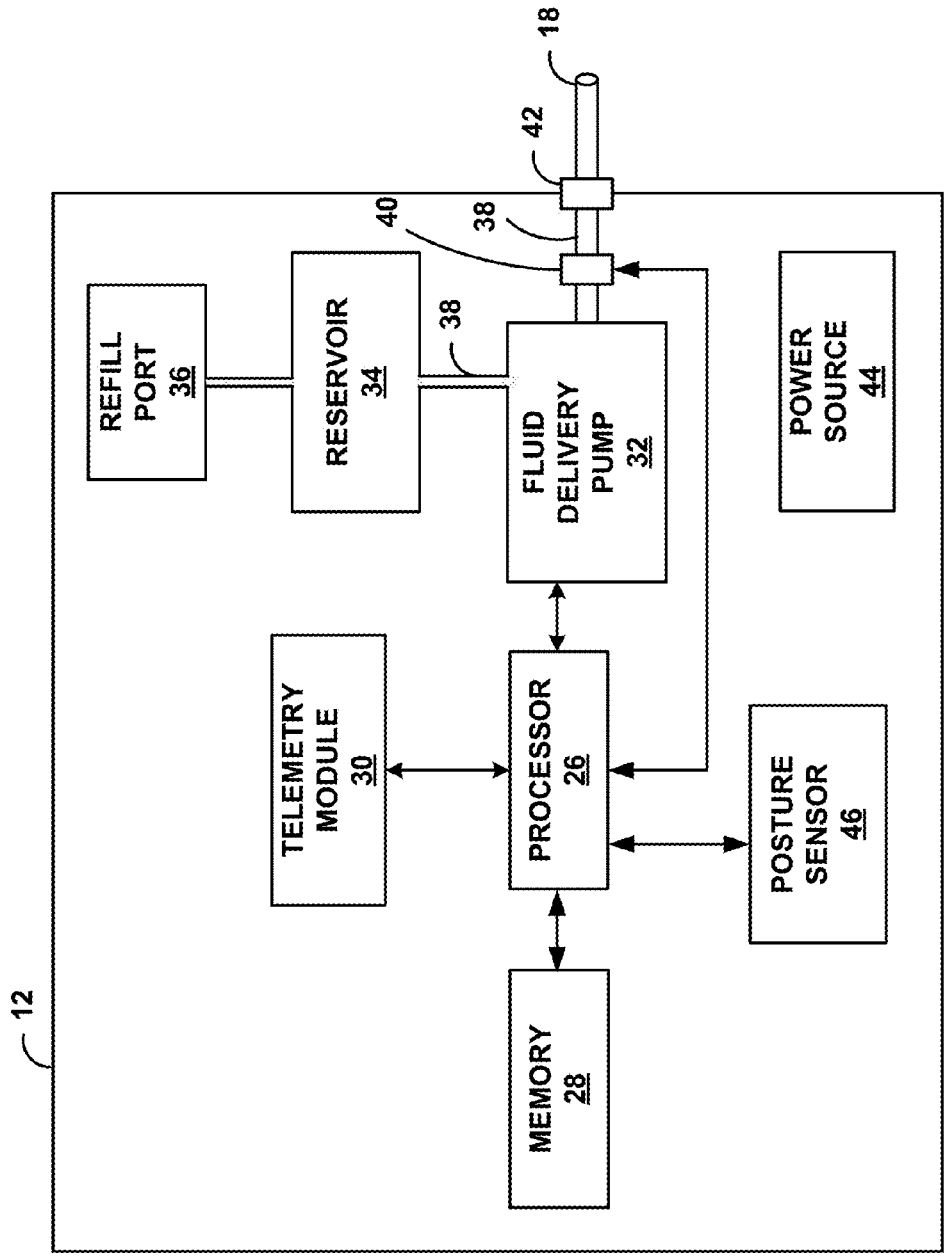
FIG. 2 is functional block diagram illustrating an example of an implantable fluid delivery device.

FIG. 2 is a functional block diagram illustrating components of an example of IMD 12, which includes processor 26, memory 28, telemetry module 30, fluid delivery pump 32, reservoir 34, refill port 36, internal tubing 38, pressure sensor 40, catheter access port 42, power source 44, and posture sensor 46. Processor 26 is communicatively connected to memory 28, telemetry module 30, fluid delivery pump 32, pressure sensor 40, and posture sensor 46. Fluid delivery pump 32 is connected to reservoir 34 and internal tubing 38. Reservoir 34 is connected to refill port 36. Pressure sensor 40 is arranged in internal tubing 38 between pump 32 and catheter access port 42. Measurements obtained by pressure sensor 40 may be received by processor 26 and stored in memory 28 by processor 26. Catheter access port 42 is connected to internal tubing 38 and catheter 18. IMD 12 also includes power source 44, which is configured to deliver operating power to various components of the IMD.

During operation of IMD 12, processor 26 controls fluid delivery pump 32 with the aid of instructions associated with program information that is stored in memory 28 to deliver a therapeutic agent to patient 16 via catheter 18. Instructions executed by processor 26 may, for example, define dosing programs that specify the amount of a therapeutic agent that is delivered to a target tissue site within patient 16 from reservoir 30 via catheter 18. The instructions may further specify the time at which the agent will be delivered and the time interval over which the agent will be delivered. The amount of the agent and the time over which the agent will be delivered are a function of, or alternatively determine, the dosage rate at which the fluid is delivered. The therapy programs may also include other therapy parameters, such as the frequency of bolus delivery, the type of therapeutic agent delivered if IMD 12 is configured to deliver more than one type of therapeutic agent, and so forth. Components described as processors within IMD 12, external programmer 20, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Upon instruction from processor 26, fluid delivery pump 32 draws fluid from reservoir 34 and pumps the fluid through internal tubing 38 to catheter 18 through which the fluid is delivered to patient 16 to effect one or more of the treatments described above. Internal tubing 38 is a segment of tubing or a series of cavities within IMD 12 that run from reservoir 34, around or through fluid delivery pump 32 to catheter access port 42. Fluid delivery pump 32 can be any mechanism that delivers a therapeutic agent in some metered or other desired flow dosage to the therapy site within patient 16 from reservoir 30 via implanted catheter 18.

In one example, fluid delivery pump 32 can be an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16. In another example, fluid delivery pump 32 can be a squeeze pump that squeezes internal tubing 38 in a controlled manner, e.g., such as a peristaltic pump, to progressively move fluid from reservoir 34 to the distal end of catheter 18 and then into patient 16 according to parameters specified by a set of program information stored on memory 28 and executed by processor 26. Fluid delivery pump 32 can also be an axial pump, a centrifugal pump, a pusher plate, a piston-driven pump, or other means for moving fluid through internal tubing 38 and catheter 18.

Periodically, fluid may need to be supplied transcutaneously to reservoir 34 because all of a therapeutic agent has been or will be delivered to patient 16, or because a clinician wishes to replace an existing agent with a different agent, or similar agent with different concentrations of therapeutic ingredients. Refill port 36 can therefore comprise a self-sealing membrane to prevent loss of therapeutic agent delivered to reservoir 30 via refill port 36. For example, after a percutaneous delivery system, e.g., a hypodermic needle, penetrates the membrane of refill port 36, the membrane may seal shut when the needle is removed from refill port 36.

Pump 32 may deliver fluid in controlled pulses. When pump 32 is called upon by processor 26 to deliver a fluid dose through catheter 18, processor 26 may also control pressure sensor 40 to measure a pressure pulse within catheter 18 that is generated by the delivery of fluid through catheter 18. Pressure sensor 40 can also measure a steady state baseline pressure within catheter 18 when no fluid dose is being delivered to patient 16, e.g., the signature baseline level. As will be discussed in greater detail below, pressure sensor 40 can be any of a number of types of sensors that are capable of measuring the pressure within an implantable catheter including, e.g., capacitive and inductive pressure sensors.

Pressure sensor 40 can read either gauge or absolute pressure of the fluid in catheter 18. Because methods disclosed herein rely on comparison of pressure just prior to and during delivery of a fluid dose to a patient through the catheter 18, changes in ambient pressure may be of reduced importance in implementing examples according to this disclosure, especially where the successive pulses are delivered within relatively short time frames, e.g., within minutes or even seconds of each other.

In those instances where it is desirable to use pressure measurements from sensor 40 that are adjusted to account for ambient pressure outside of the catheter 18, a reference pressure may be detected within the body of patient 16 in which catheter 18 is implanted or may be detected outside of the patient's body. When detected within the body of patient 16, a reference pressure may be detected in a location near IMD 12 or the target delivery site near distal end 18B of catheter 18, or even in a location in a separate area of the patient's body. A reference pressure may be obtained in any location capable of providing a pressure indicative of the external environment of implanted catheter 18.

In one example, an infusion system may include a catheter 18 having a lumen for delivering fluid. The lumen may be used to obtain reference pressures when fluid is delivered through it and when no fluid is delivered. In another example, the catheter may have a first lumen for delivering a fluid and a second lumen through which no fluid is delivered. A reference pressure may then be detected in the second lumen. The second lumen in catheter 18 can be used to obtain a reference pressure from distal end 18B of catheter 18, from a region near the target delivery site of therapy system 10. An explanation of reference pressures may be found in commonly-assigned U.S. Pat. No. 7,320,676, entitled "PRESSURE SENSING IN IMPLANTABLE MEDICAL DEVICES," which issued on Jan. 22, 2008 to Miesel, the entire contents of which being incorporated herein by reference.

The pressure pulse(s) measured by pressure sensor 40 during delivery of a fluid dose to patient 16 can be stored in memory 28. Processor 26 can access one or more stored pressure pulses to determine baseline pressure decay of catheter 18 based on an algorithm, group of algorithms, or a series of executable steps in any form, which may also be stored in memory 28. Processor 26 may also rely on one or more look-up tables, or other data aggregations stored in memory 28 to determine baseline pressure decay of catheter 18. For example, processor 26 may retrieve stored pressure pulses from a look-up table in memory 28. Memory 28 may include any volatile or non-volatile media, such as a random access memory (RAM), read only memory (ROM), non-volatile RAM (NVRAM), electrically erasable programmable ROM (EEPROM), flash memory, and the like.

Although controlling fluid pump 32 and sensor 40 to deliver fluid through catheter 18 and measure pressure therein has been described as executed by IMD 12, and in particular, processor 26, in other examples one or more of these functions may be carried out by other devices including, e.g., external programmer 20. For example, a user may interact with external programmer 20 to command processor 26 of IMD 12 to control fluid pump 32 to deliver a fluid dose to patient 16 through catheter 18. Thereafter, pressure sensor 40 may measure pressure associated with catheter 18 during delivery of the fluid dose and processor 26 may control telemetry module 30 to transmit the measured pressure data to external programmer 20. The pressure associated with the catheter may be a pressure in the catheter, or in any element in communication (e.g., fluid communication) with the catheter, such as any conduit in communication with the catheter and/or the pump through which the pump delivers a therapeutic agent, e.g., internal tubing 38. External programmer 20 may, in some cases, store the measured pressure data in one or more non-volatile memories included in the programmer. In any event, a processor housed within programmer 20 may determine the baseline pressure decay profile of catheter 18 and therefore a determination of catheter patency based on the measured pressure decay profile received from IMD 12 in accordance with the techniques described below.

In addition to storing pressure pulse measurement data obtained by pressure sensor 40 and one or more algorithms used to execute example methods according to this disclosure, memory 28 may store program information including instructions for execution by processor 26, such as, but not limited to, therapy programs, historical therapy programs, timing programs for delivery of fluid from reservoir 34 to catheter 18, and any other information regarding therapy of patient 16. A program may indicate the bolus size or flow rate of the drug, and processor 26 may accordingly deliver therapy. A program may also indicate the frequency at which pressure sensor 40 is commanded to measure a pressure pulse and, as will be discussed in greater detail below, instructions for determining patency of catheter 18 based on one or more measured pressure pulses.

Posture sensor 46 may comprise, for example, an accelerometer (e.g., multi-axis accelerometer), or any other device capable of detecting changes in orientation of the patient's body. Posture sensor 46 may be capable of determining, based on sensed changes in orientation of patient's body, a posture associated with the patient (e.g., lying down, upright, sitting, reclining, and the like). Additionally, posture sensor 46 may be capable of determining an activity in which the patient is engaging, e.g., walking. Posture sensor 46 may be coupled to processor 26. In one example, processor 26 may instruct posture sensor 46 to determine a posture associated with the patient when a pressure measurement is obtained. In this manner, processor 26 may associate a measured pressure with a posture. In one example, a pressure baseline may be determined and associated with a posture indicated by posture sensor 46, such that subsequent pressure measurements may be compared to pressure baseline associated with the same posture as that sensed when the subsequent pressure measurement is obtained.

Memory 28 may include separate memories for storing instructions, patient information, therapy parameters (e.g., grouped into sets referred to as "dosing programs"), therapy adjustment information, program histories, and other categories of information such as any other data that may benefit from separate physical memory modules. Therapy adjustment information may include information relating to timing, frequency, rates and amounts of patient boluses or other permitted patient modifications to therapy. In some examples, memory 28 stores program instructions that, when executed by processor 26, cause IMD 12 and processor 26 to perform the functions attributed to them in this disclosure.

At various times during the operation of IMD 12 to treat patient 16, communication to and from IMD 12 may be necessary to, e.g., change therapy programs, adjust parameters within one or more programs, configure or adjust a particular bolus, send or receive an estimated length of catheter 18, or to otherwise download information to or from IMD 12. Processor 26 therefore controls telemetry module 30 to wirelessly communicate between IMD 12 and other devices including, e.g. programmer 20. Telemetry module 30 in IMD 12, as well as telemetry modules in other devices described herein, such as programmer 20, can be configured to use RF communication techniques to wirelessly send and receive information to and from other devices respectively. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply could transcutaneously power IMD 12 as needed or desired.

Figure 3:
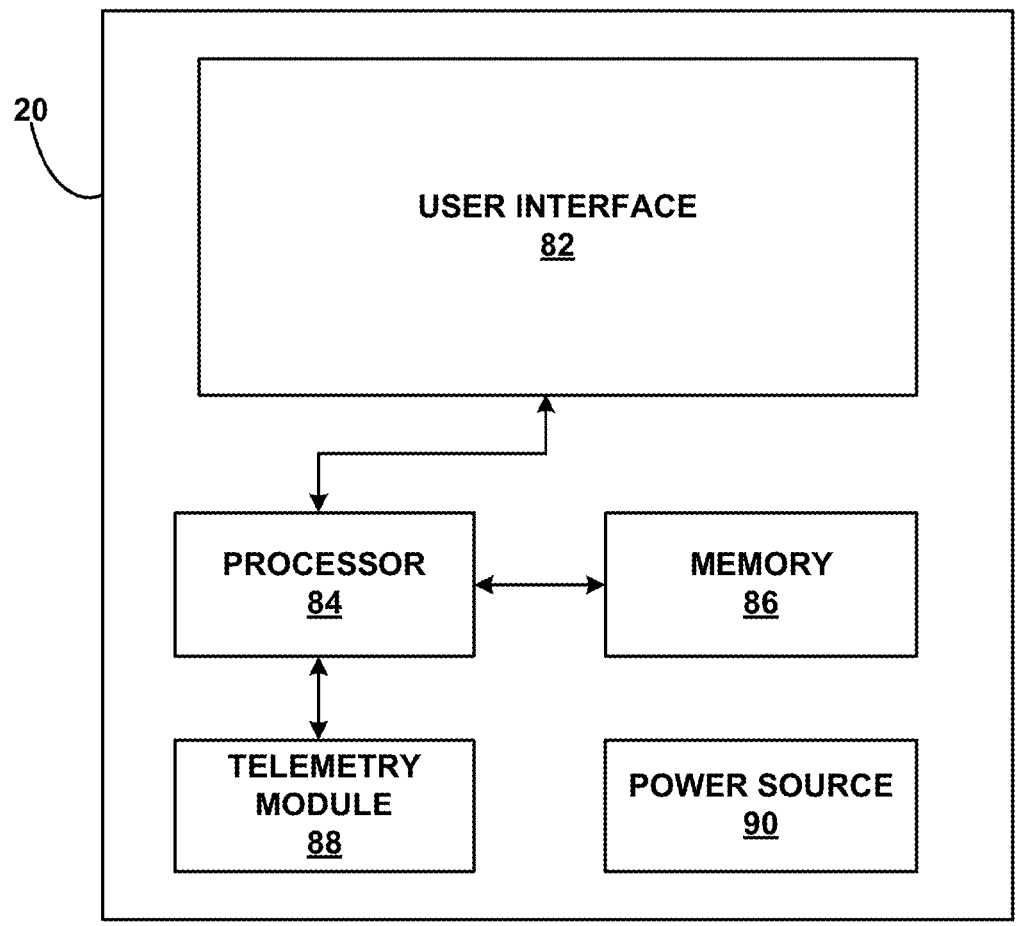
FIG. 3 is a functional block diagram illustrating various components of an external programmer for an implantable medical device.

FIG. 3 is a functional block diagram illustrating various components of an external programmer 20 for IMD 12. As shown in FIG. 3, external programmer 20 includes processor 84, memory 86, telemetry module 88, user interface 82, and power source 90. A clinician or patient 16 interacts with user interface 82 in order to manually change the parameters of a dosing program, change dosing programs within a group of programs, view therapy information, view historical therapy regimens, establish new therapy regimens, select programming tasks, or otherwise communicate with IMD 12 or view programming information.

User interface 82 may include a screen and one or more input buttons, as discussed in greater detail below, that allow external programmer 20 to receive input from a user. Alternatively, user interface 82 may additionally or only utilize a touch screen display. The screen may be a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, programmer 20 may further include one or more audio speakers, voice synthesizer chips, piezoelectric buzzers, or the like.

Input buttons for user interface 82 may include a touch pad, increase and decrease buttons, emergency shut off button, and other buttons needed to control the therapy, as described above with regard to patient programmer 20. Processor 84 controls user interface 82, retrieves data from memory 86 and stores data within memory 86. Processor 84 also controls the transmission of data through telemetry module 88 to IMD 12. The transmitted data may include therapy program information specifying various drug delivery program parameters. Memory 86 may include operational instructions for processor 84 and data related to therapy for patient 16.

User interface 82 may be configured to present therapy program information to the user. User interface 82 enables a user to program IMD 12 in accordance with one or more dosing programs, therapy schedules, or the like. As discussed in greater detail below, a user such as a clinician, physician or other caregiver may input patient information, drug information, therapy schedules, priming information, bridging information, drug/IMD implant location information, or other information to programmer 20 via user interface 82. In addition, user interface 82 may display therapy program information as graphical bar graphs or charts, numerical spread sheets, or in any other manner in which information may be displayed. Further, user interface 82 may present nominal or suggested therapy parameters that the user may accept via user interface 82.

User interface 82 may be configured to display a location of IMD 12 within patient 16, as well as a location of fluid within IMD 12. User interface 82 may display a representation of the location of the fluid overlaid with a representation of IMD 12. The representation may be a graphical representation. In some cases, the graphical representation may be a pictorial representation. As described in greater detail herein, user interface 82 may display information and menus for the user to select from to set up a determination of the baseline pressure of the catheter. For example, the user may select menu items and enter information on the user interface 82 to instruct the IMD to take pressure measurements so that baseline pressure decay is displayed for the user to make a determination regarding the catheter patency, and to perform further troubleshooting of the catheter and/or pump.

Telemetry module 88 allows the transfer of data to and from IMD 12. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Power source 90 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to or from IMD 12. In this manner, the recharging device may be able to act as an intermediary communication device between external programmer 20 and IMD 12. The techniques described in this disclosure may be communicated between IMD 12 via any type of external device capable of communication with IMD 12.

Figure 4:
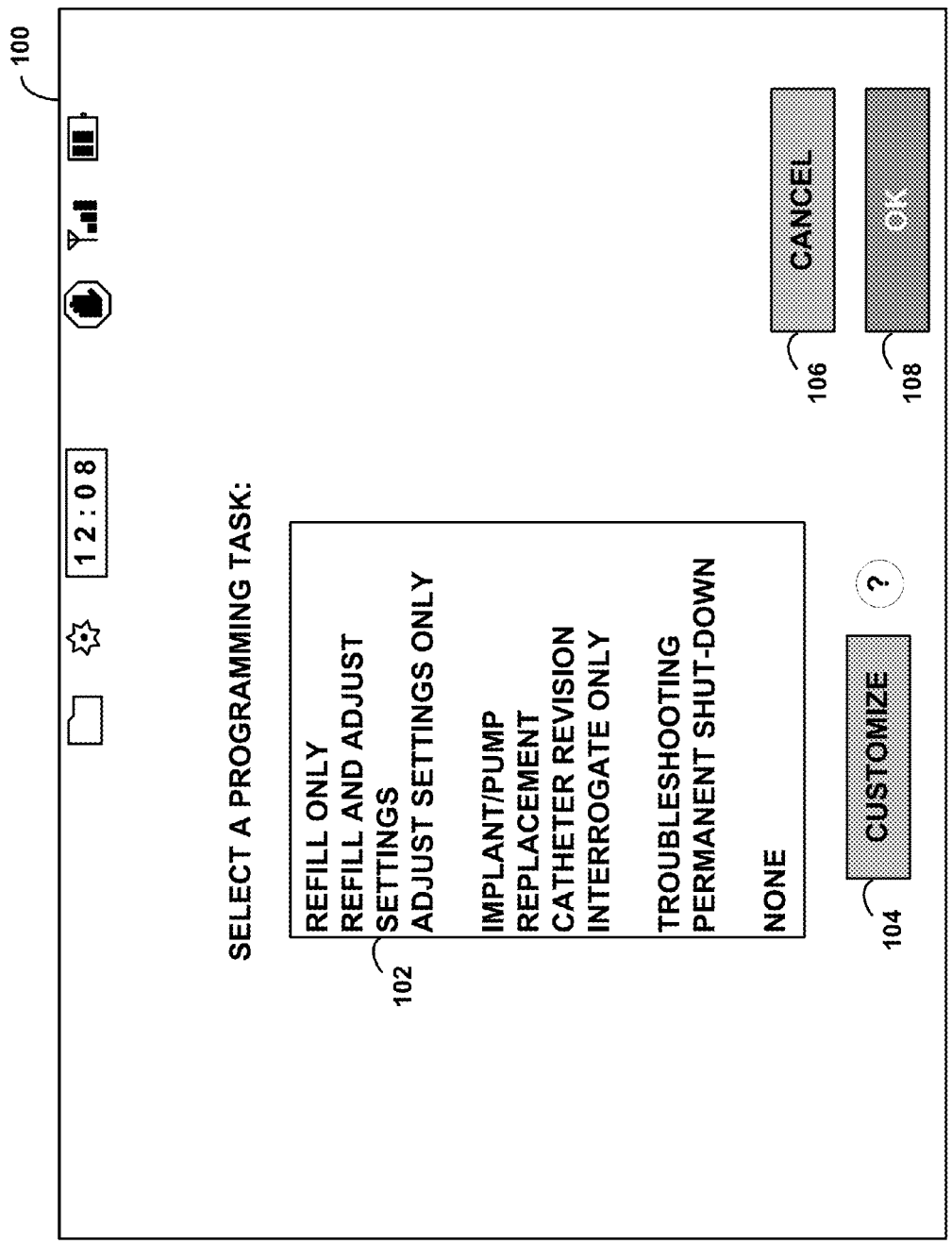
FIG. 4 is a screenshot illustrating an example user interface screen presented by a programmer when a user initiates interaction with the programmer.

FIG. 4 is a screenshot illustrating an example user interface screen 100 presented by programmer 20 when a user initiates interaction with programmer 20. User interface screen 100 may be displayed by user interface 82 of programmer 20, and may present a task-oriented programming interface. When a user begins a session of working with programmer 20, programmer 20 presents user interface screen 100 to the user via user interface 82. The user may select from a variety of tasks 102 to perform using programmer 20. Tasks 102 of FIG. 4 depict example tasks "refill only," "refill and adjust settings," "adjust settings only," "implant/pump replacement," "catheter revision," "interrogate only," "troubleshooting," "permanent shut-down," and "none." Other examples may include additional or fewer tasks for the user to perform. For example, if programmer 20 is a patient programmer, a different list of tasks may be displayed and may include limited actions that a patient can perform using a patient programmer.

In one example, processor 84 (FIG. 3) determines, from the selection of tasks 102, a series of task screens to present to the user of programmer 20 via user interface 82. Processor 84 may cause user interface 82 to present one or more task screens, each of which may receive one or more pieces of data from the user, in order to program IMD 12 according to the selected one of tasks 102. Programmer 20 may implement more task screens than are necessary for any one of tasks 102, and therefore, programmer 20 may not display unnecessary screens to the user. In this manner, programmer 20 may assist a user in efficiently programming IMD 12 by requesting relevant data without requesting unnecessary data. Programmer 20 may therefore minimize the number of screens that are displayed based on a selection from tasks 102.

The user may select one of tasks 102 from screen 100. For example, the user may select one of the tasks using a pointer controlled by a mouse or other pointing device. As another example, the user may select one of the tasks by touching the task on a touch-screen interface, e.g., with a finger or a stylus. The user may select the "cancel" button 106 to end the current session or, after selecting one of tasks 102, the user may select the "OK" button 108 to perform the task. Upon receiving a selection of "OK" button 108, the user interface presents a different display screen to enable the user to perform the task with programmer 20. The user may also select the "customize" button 104 to customize the task selected from list 102, e.g., one or more parts or sub-parts of the task selected from list 102. In this manner, the user may select which of the one or more task screens are displayed. As shown in FIG. 4, prior to selecting a task, the "OK" button 108 may be grayed out, i.e., the user may not be able to select it.

Figure 5:
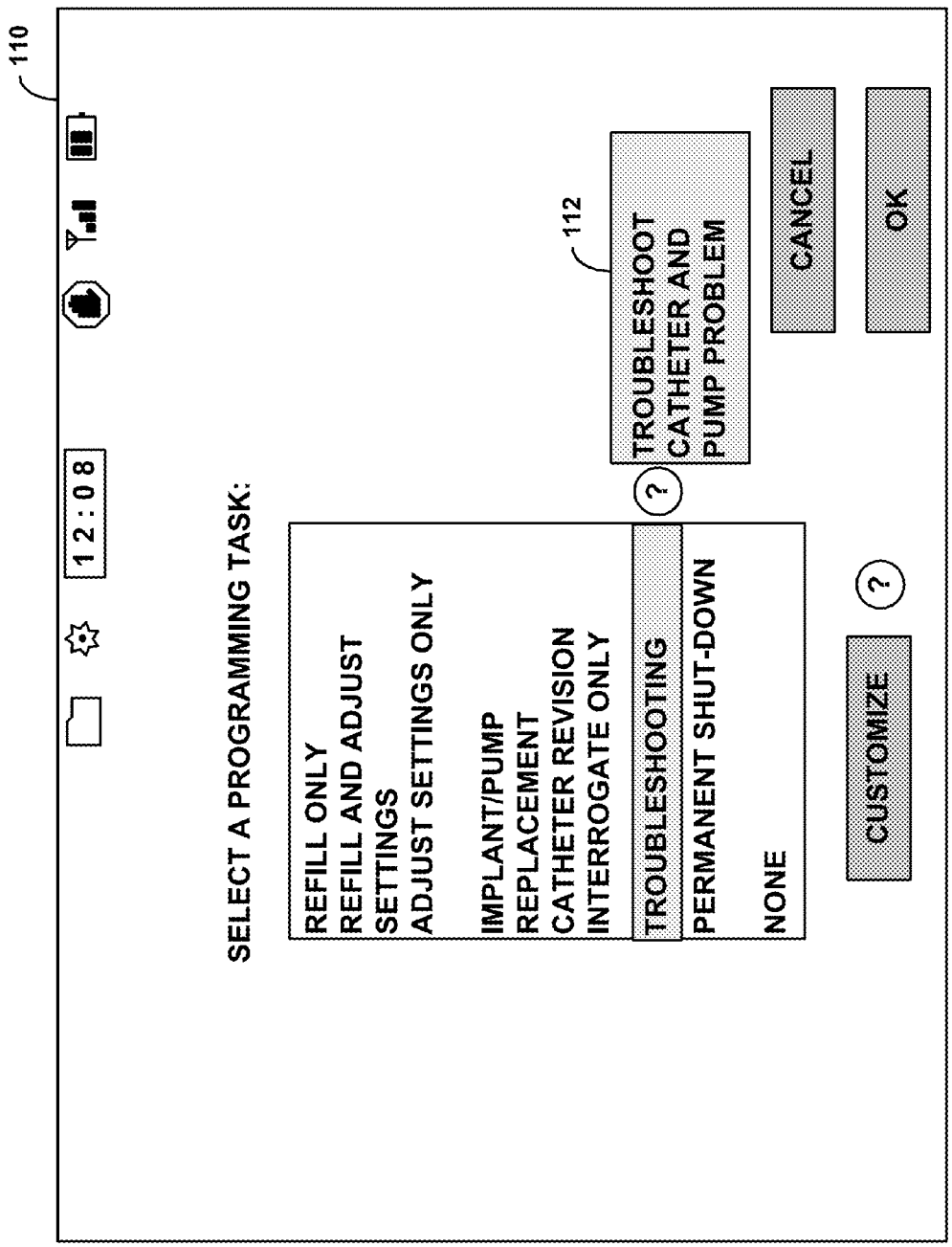
FIG. 5 is a screenshot illustrating an example user interface screen presented by a programmer when a user requests information regarding a displayed item.

FIG. 5 is a screenshot illustrating an example user interface screen 110 presented by programmer 20 when a user requests information regarding a displayed item. User interface screen 110 may be displayed by user interface 82 of programmer 20. User interface screen 110 may be displayed, for example, when a user clicks on one of the programming tasks to get more information. In this example, the user selected to get more information regarding the troubleshooting task. As a result, a window 112 pops up within the screen showing the requested information. In this example, the user may be informed of what the troubleshooting task may be used for, e.g., "troubleshoot catheter and pump problems."

Figure 6:
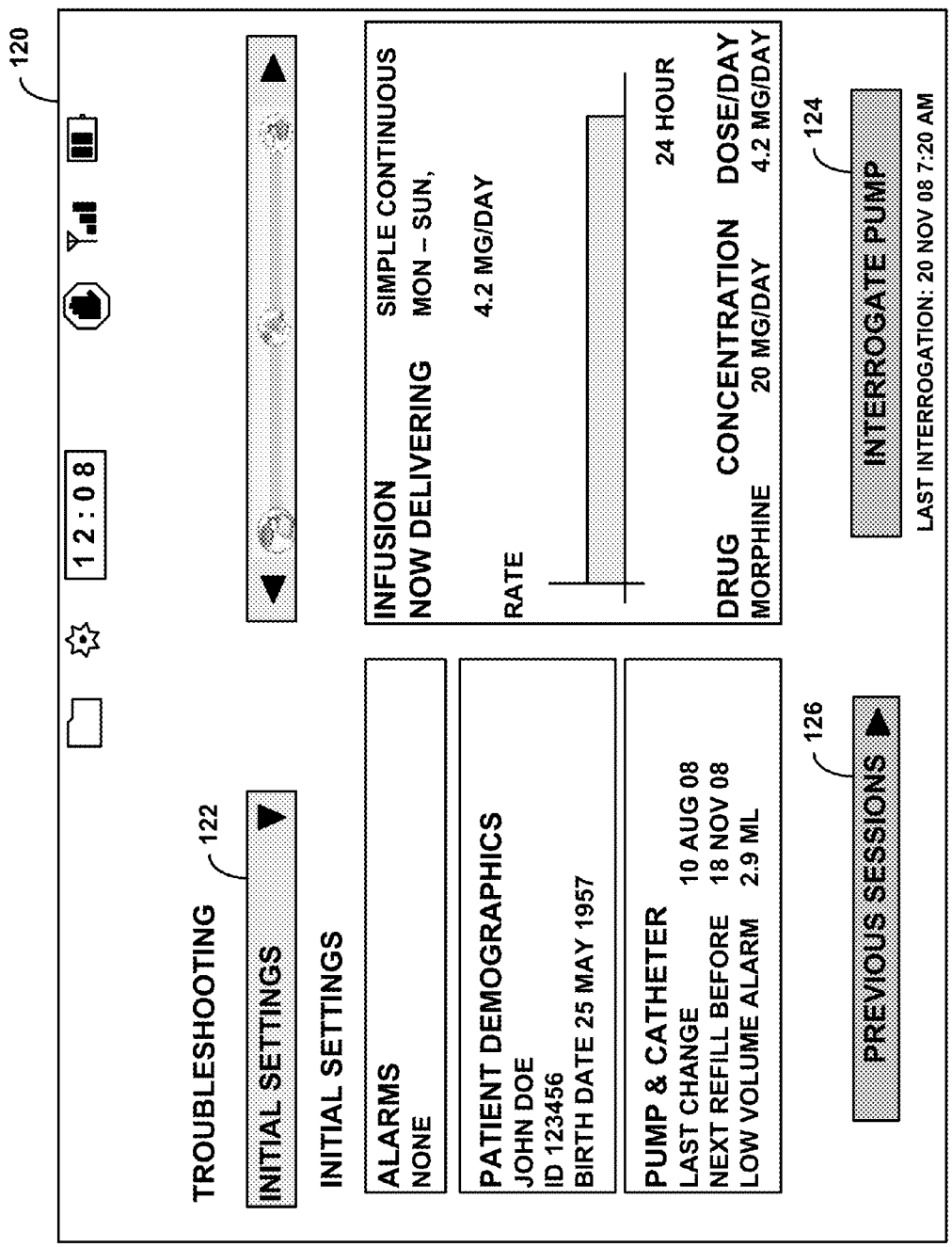
FIG. 6 is a screenshot illustrating an example user interface screen for troubleshooting an IMD.

FIG. 6 is a screenshot illustrating an example user interface screen 120 for troubleshooting IMD 12. User interface screen 120 may be displayed by user interface 82 of programmer 20. User interface screen 120 may be displayed, e.g., when a user selects the "troubleshooting" task from tasks 102 and then selects the "OK" button 108 of user interface 110 (FIG. 5). FIG. 6 depicts current therapy program information for the current settings, e.g., initial settings of an IMD, such as IMD 12 (FIG. 1), associated with the program. The initial settings may be displayed in response to selecting "initial settings" from a drop down menu 122. For example, the therapy program information may include alarms information, patient demographics information, pump and catheter information, drug information, and an infusion pattern.

In the example of FIG. 6, there is no pertinent alarm information. However, the pump and catheter information indicates when the last change occurred, when the next refill should be performed, and the volume setting for the alarm to indicate a low volume in the pump. The infusion pattern shows a rate of infusion over a selected period, e.g., 24 hour period, which in this case is a simple continuous 4.2 mg/day. In other examples, the rate of infusion may be variable over a specified period, which may be 24 hours, a week, or a month, as examples. Information regarding the drug, its concentration, and its dosage may be also displayed on the screen. The user may select "interrogate pump" button 124 to populate programmer 20 with data stored on IMD 12. For example, IMD 12 may have been programmed with a different programmer than programmer 20. The user may also select "interrogate pump" button 124 to retrieve data from IMD 12 that IMD 12 has collected during operation within patient 16. As shown in this example, information regarding the last interrogation (e.g., date and time) may be displayed below the "interrogate pump" button 124. The user may also be able to retrieve the information obtained during previous sessions by selection the "previous sessions" button 126.

Figure 7:
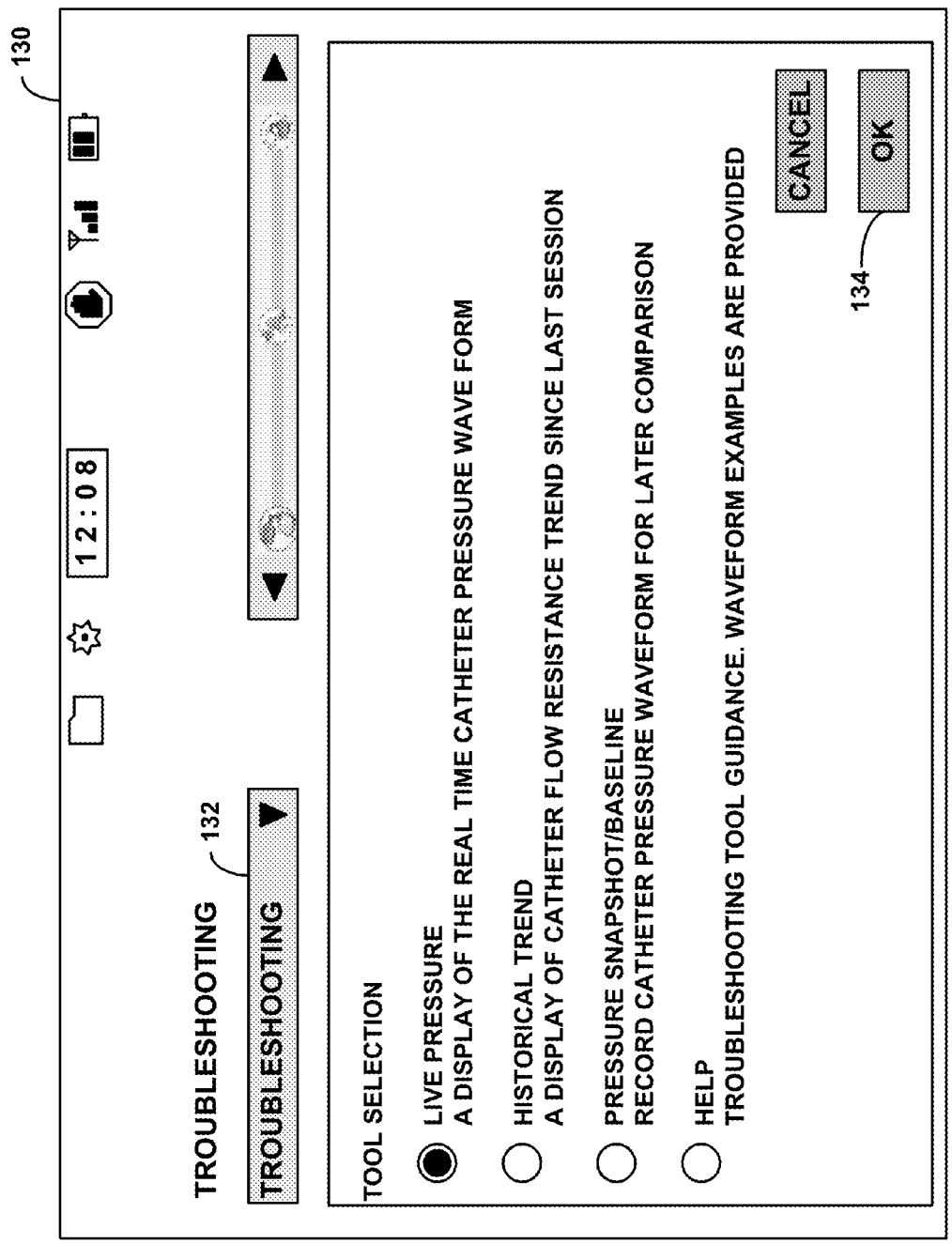
FIG. 7 is a screenshot illustrating an example user interface screen for troubleshooting an IMD.

FIG. 7 is a screenshot illustrating an example user interface screen 130 for troubleshooting IMD 12. The user may perform troubleshooting of the IMD 12 and, more specifically, of the catheter and/or pump by selecting "troubleshooting" from the drop down menu 132. FIG. 7 illustrates the options available in the selected troubleshooting function, which include "live pressure," "historical trend," "pressure snapshot/baseline," and "help," along with an explanation of what each of the functions is. For example, the "live pressure" function provides a display of real-time catheter pressure waveform, the "historical trend" function provides a display of catheter flow resistance trend since the previous session, the "pressure snapshot/baseline" function records catheter pressure waveform for later comparison, and the "help" function provides the user with troubleshooting tool guidance and examples of waveforms. When a user selects any of these options and clicks the "OK" button 134, the user interface switches to a screen associated with that selection. In this example, the user had selected the "live pressure" function, which as indicated on the screen will allow the user to see a display of the real time catheter pressure waveform, as will be described in more detail below.

Figure 8A:
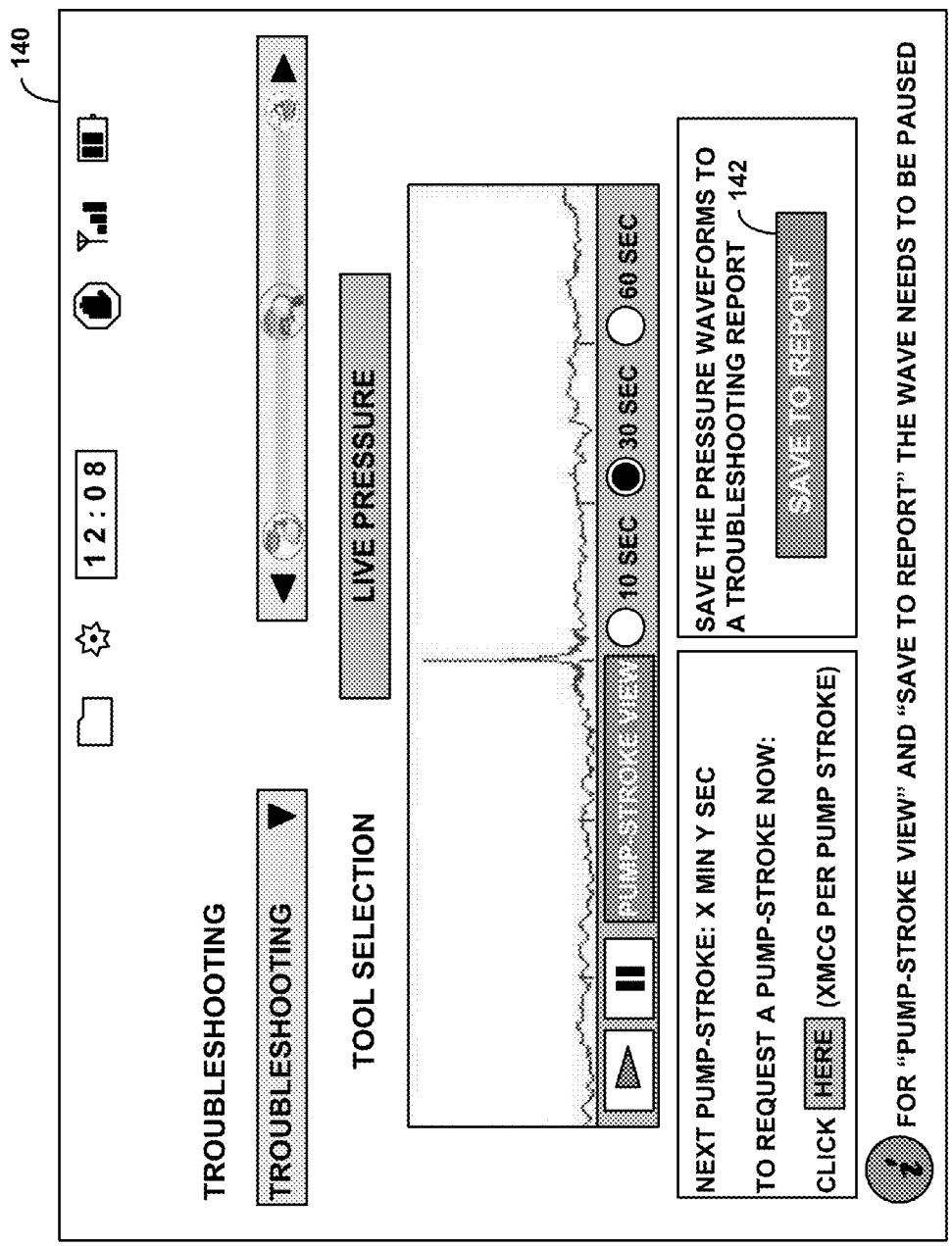
FIGS. 8A-8O are screenshots illustrating an example user interface for troubleshooting using live pressure selection.
Figure 8B:
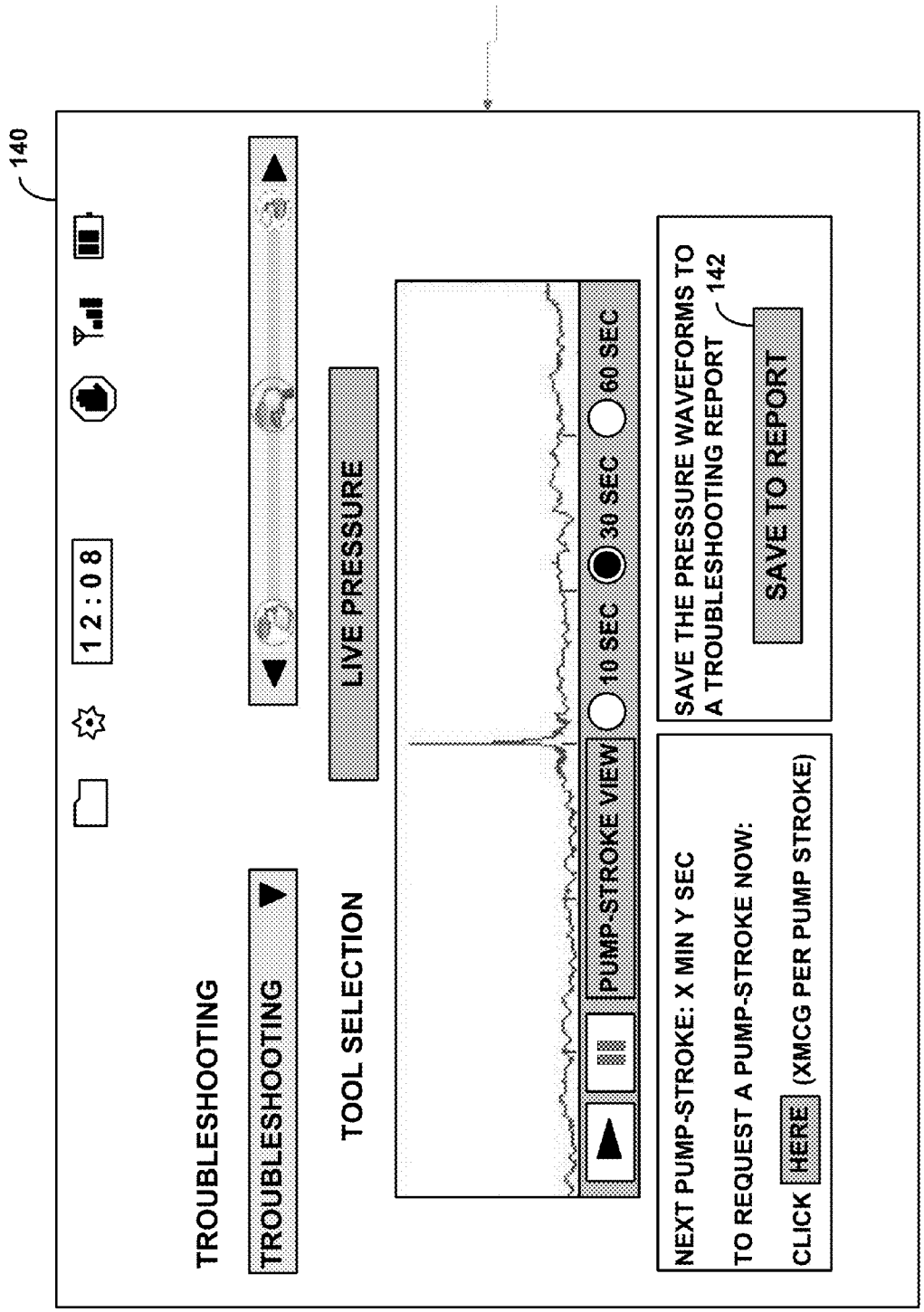
Figure 8C:
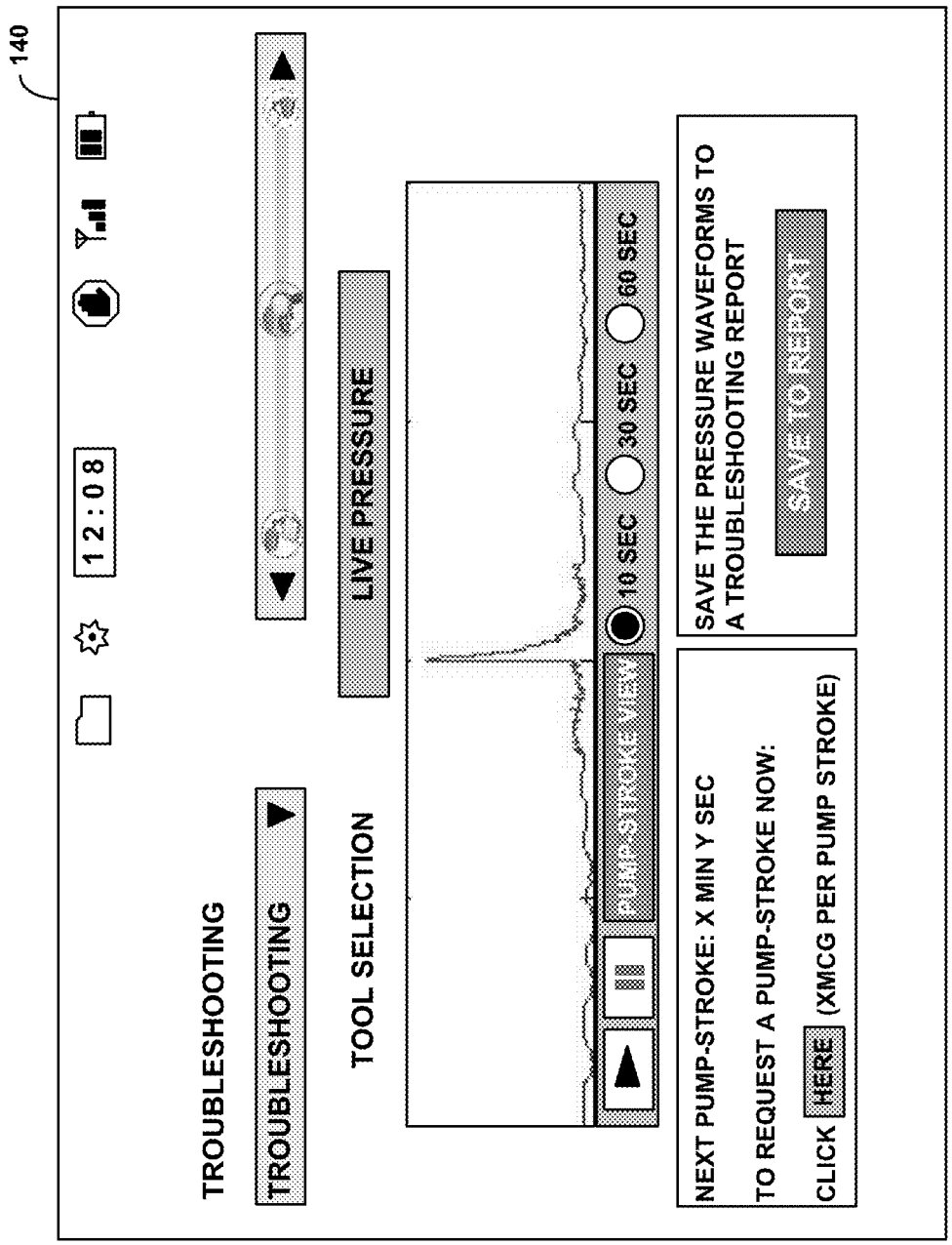
Figure 8D:
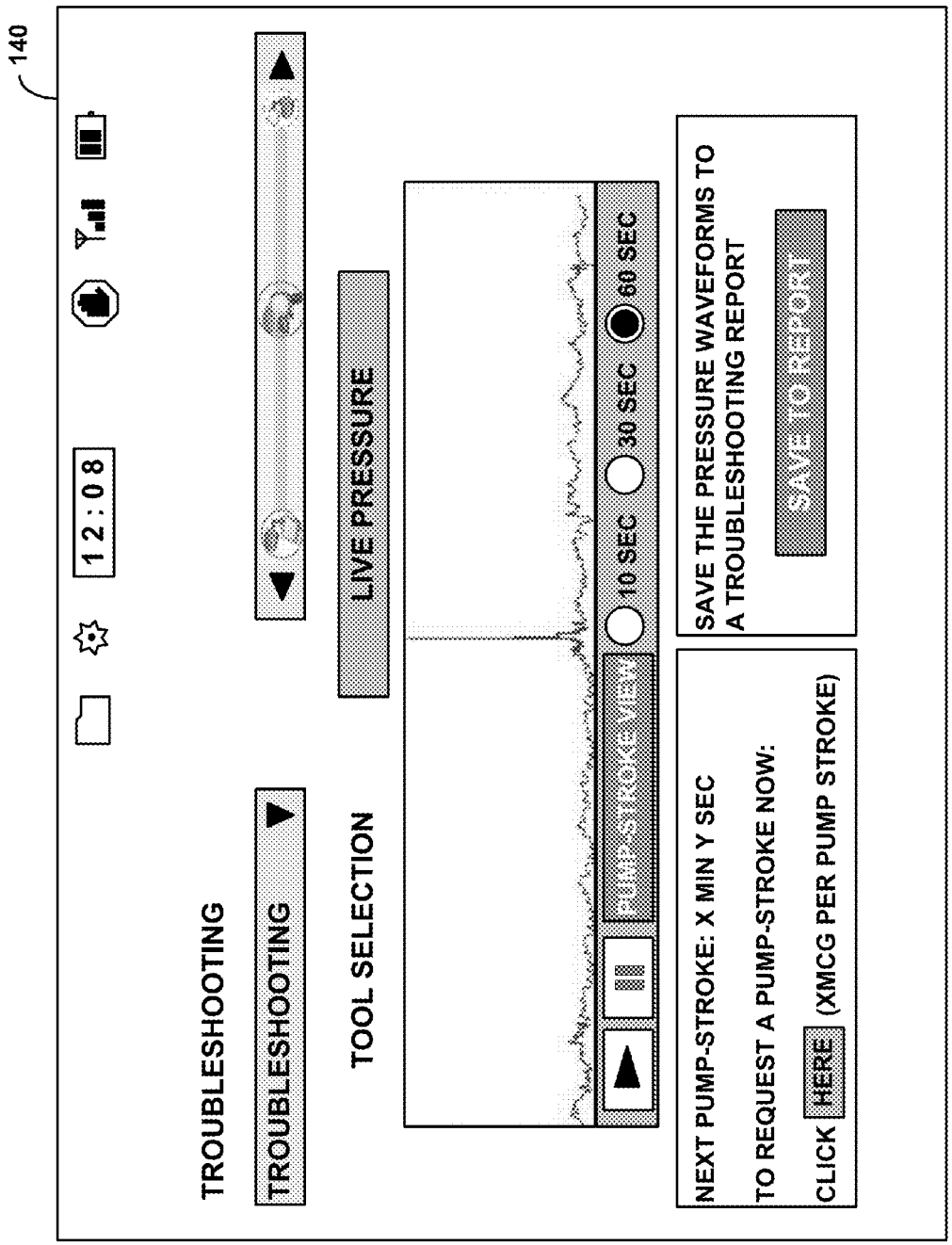
Figure 8E:
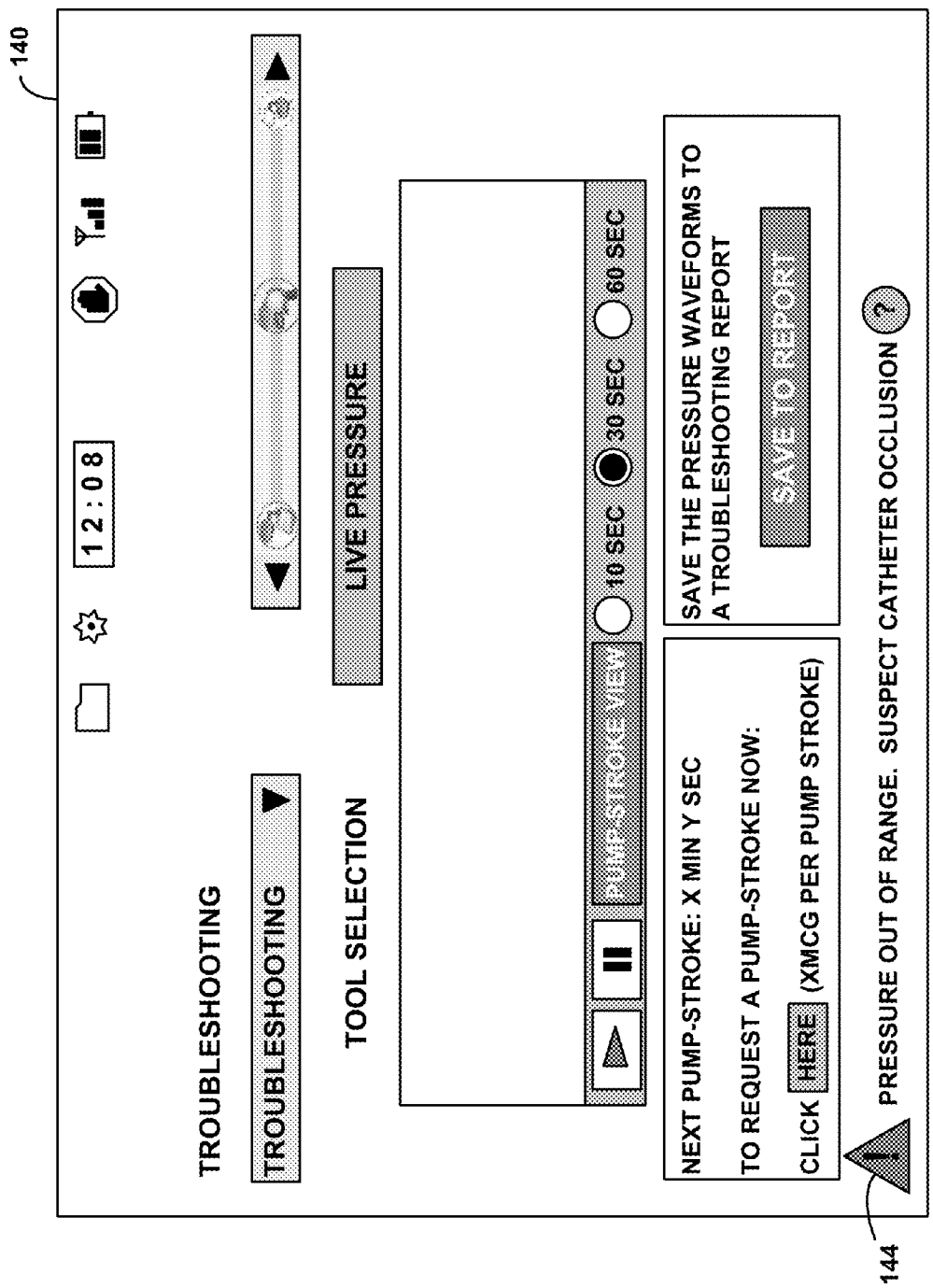
Figure 8F:
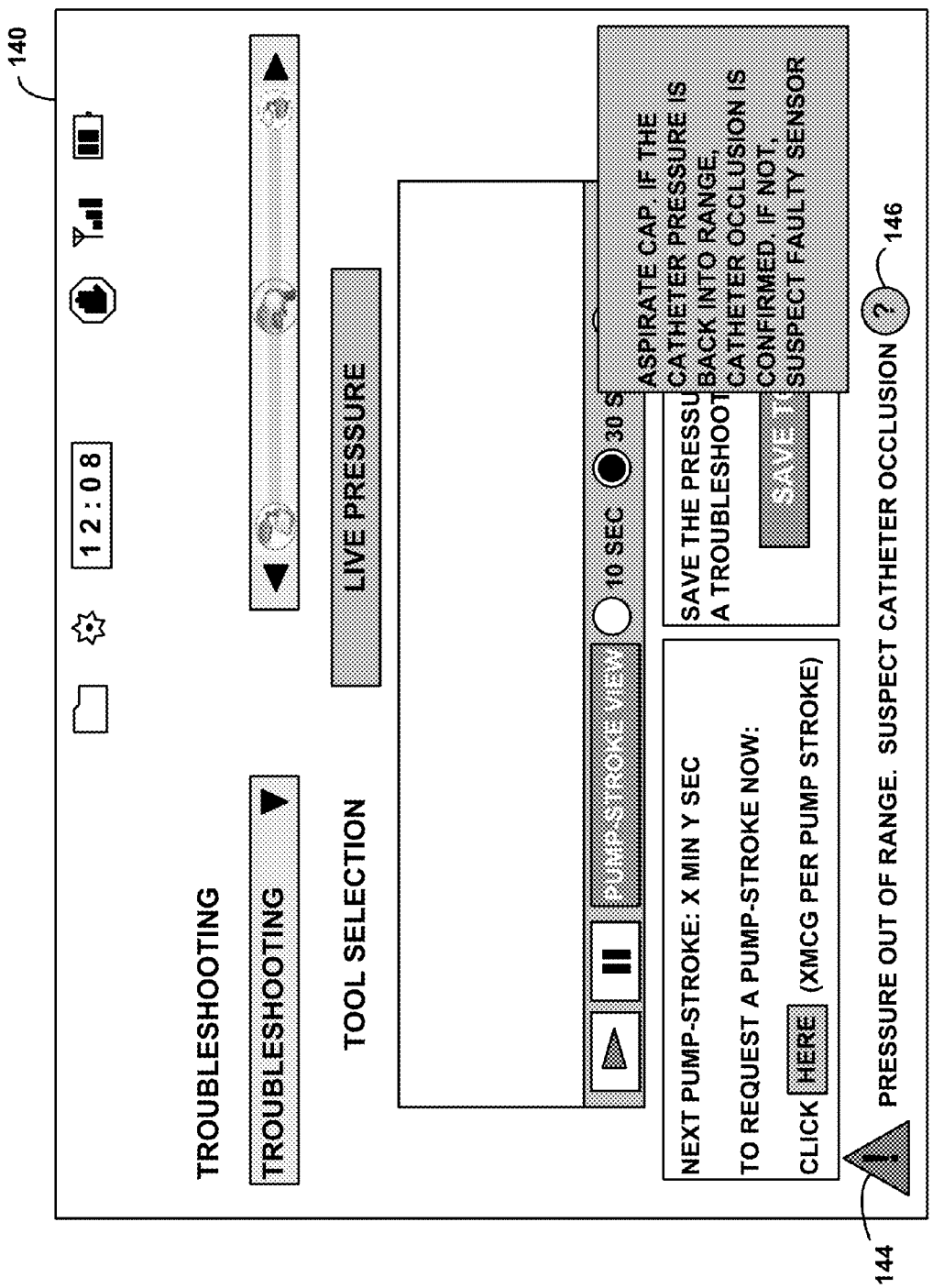
Figure 8G:
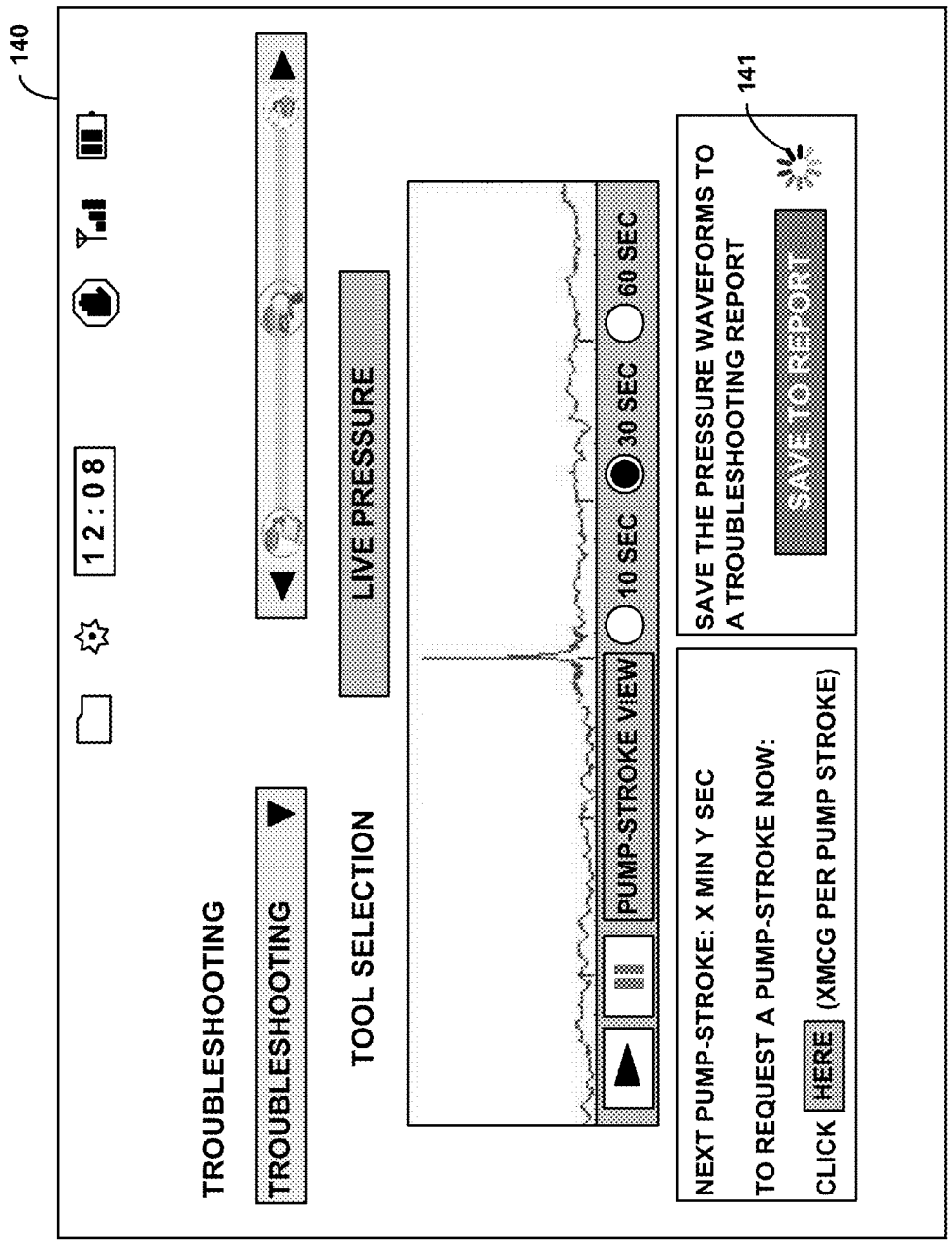
Figure 8H:
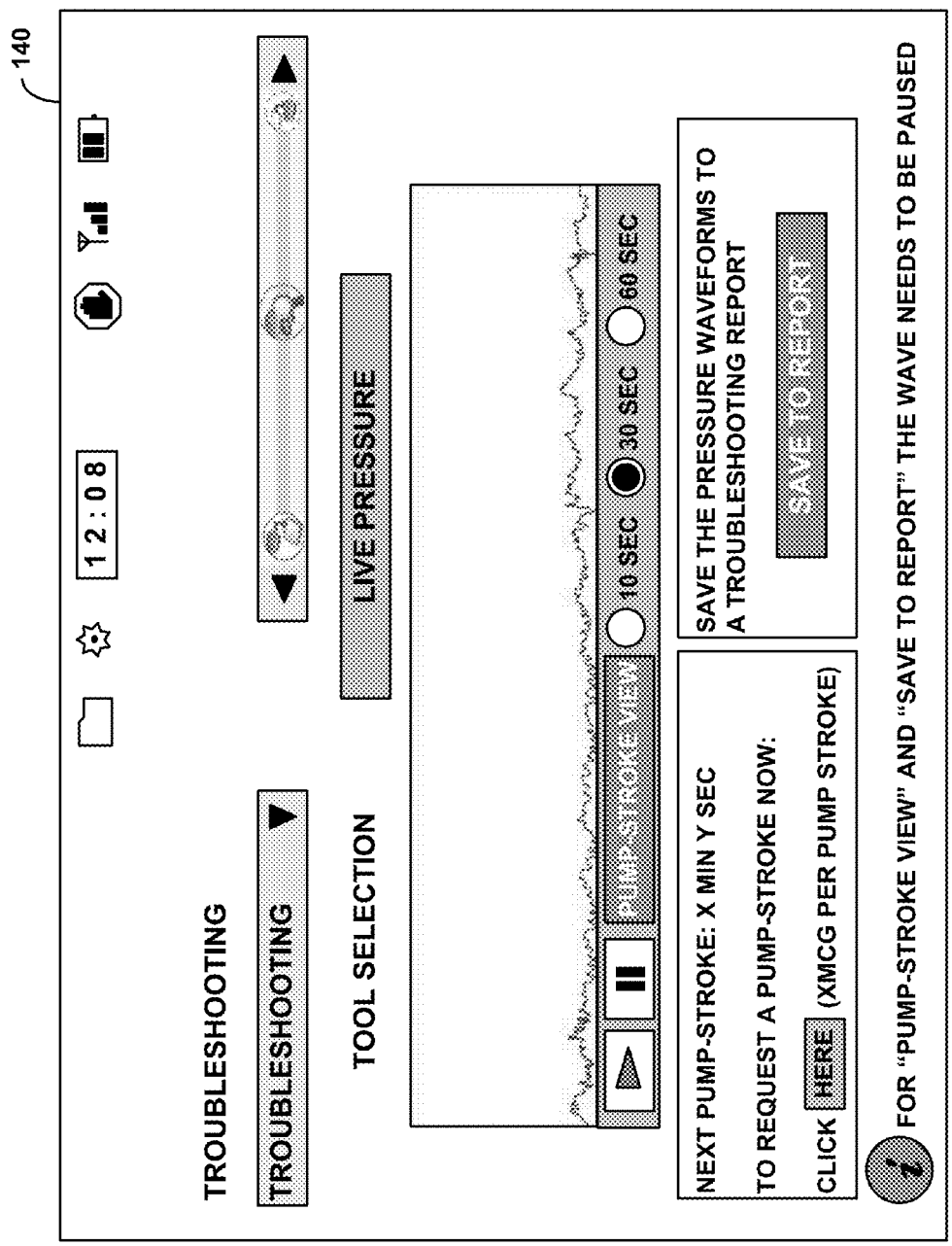
Figure 8I:
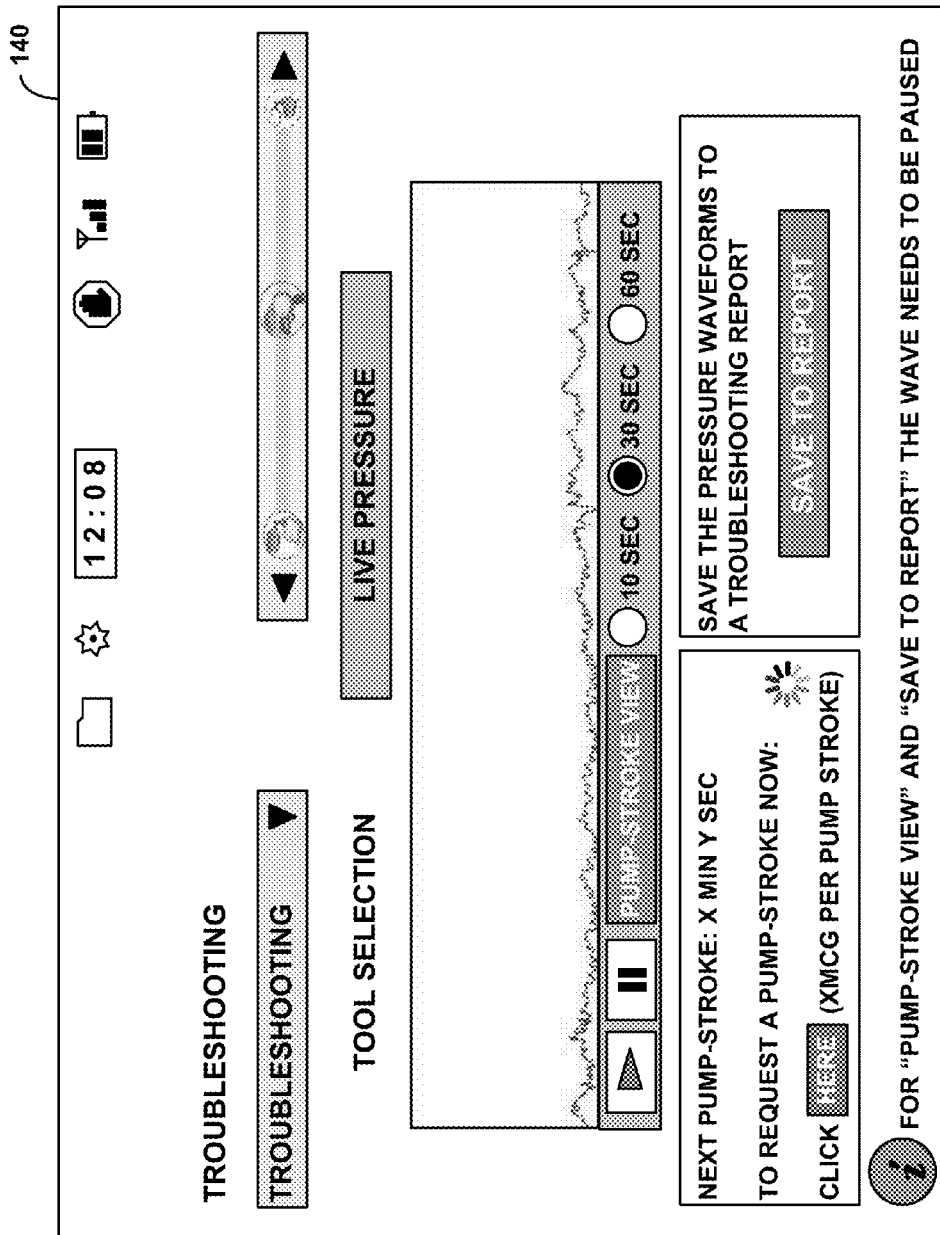
Figure 8J:
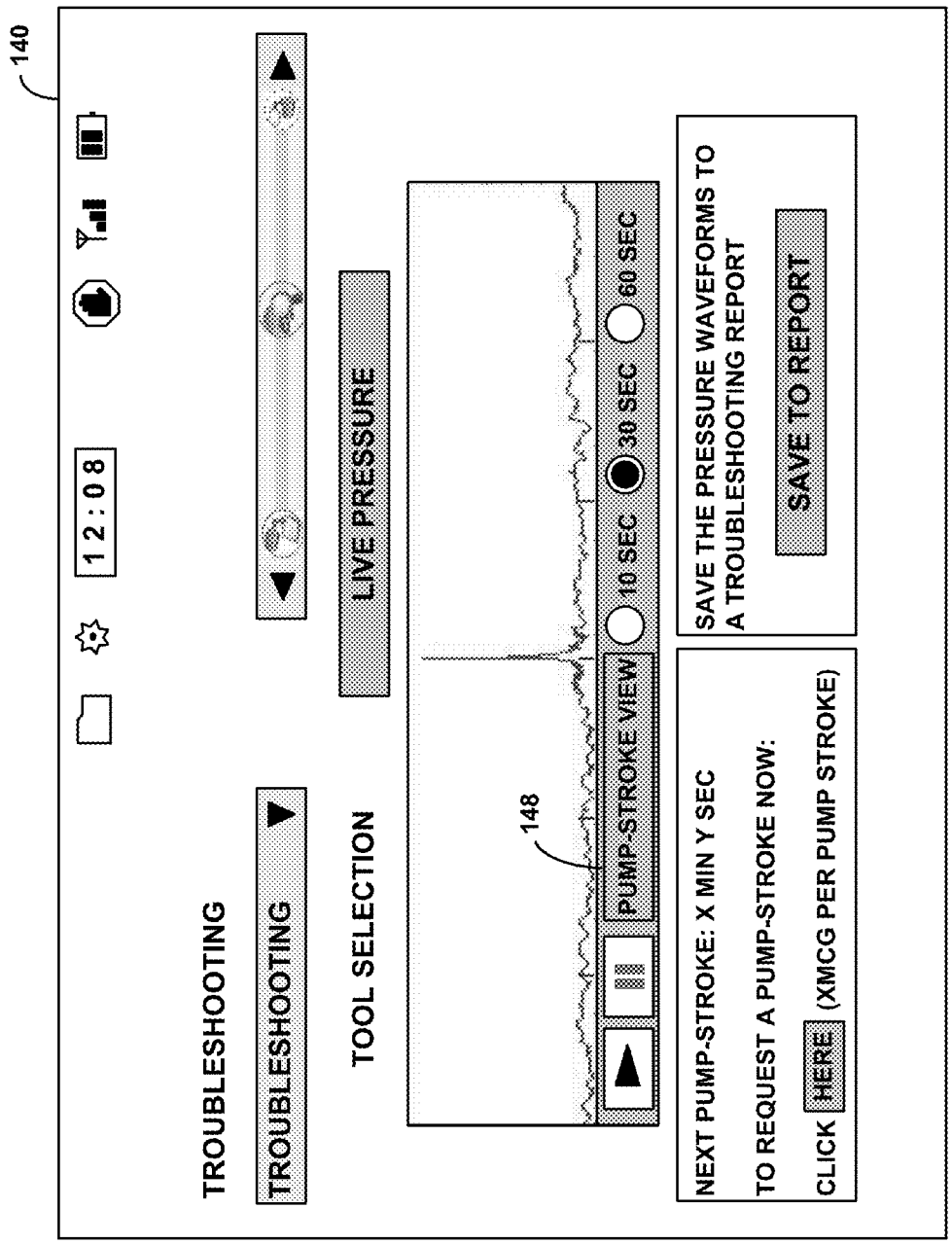
Figure 8K:
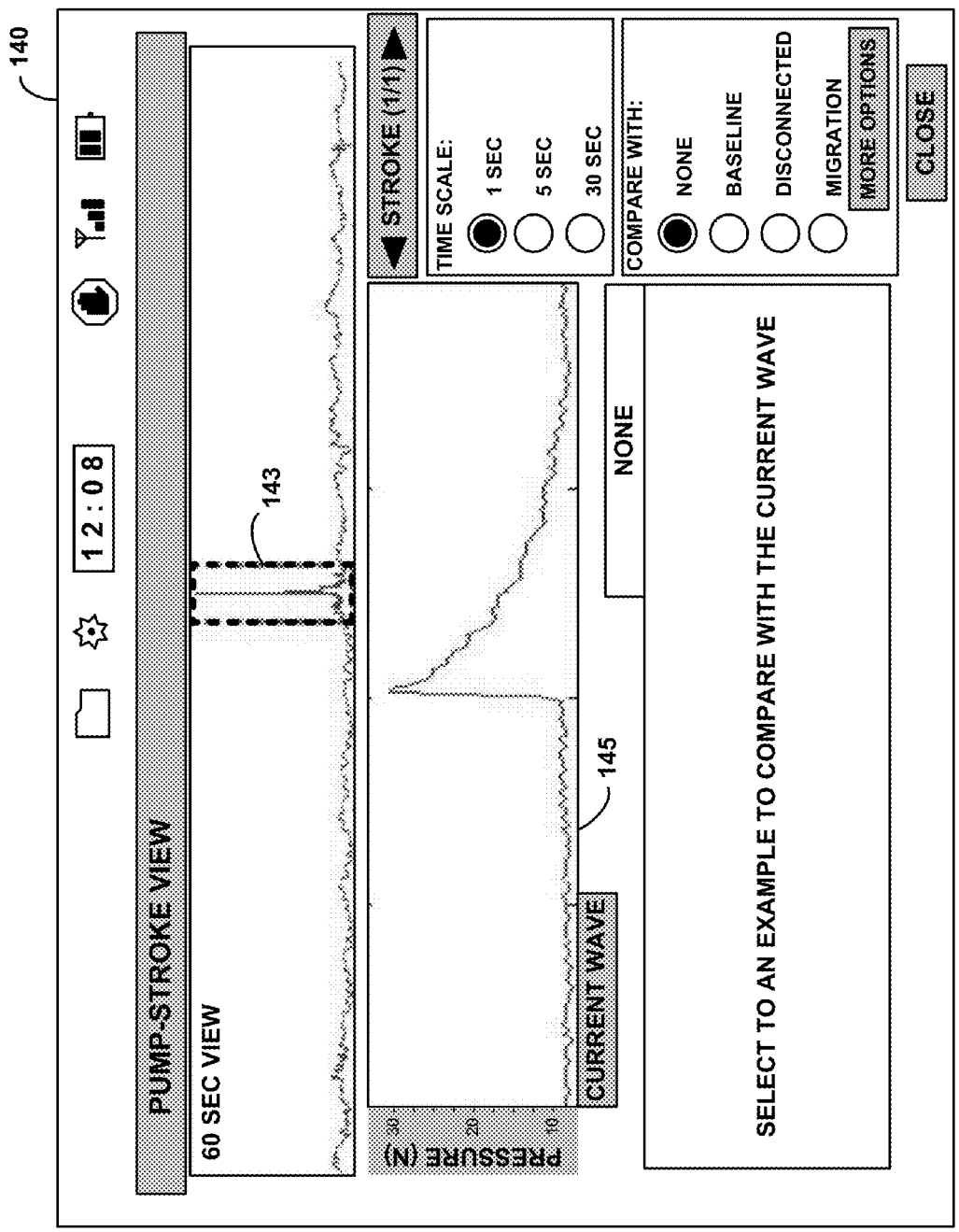
Figure 8L:
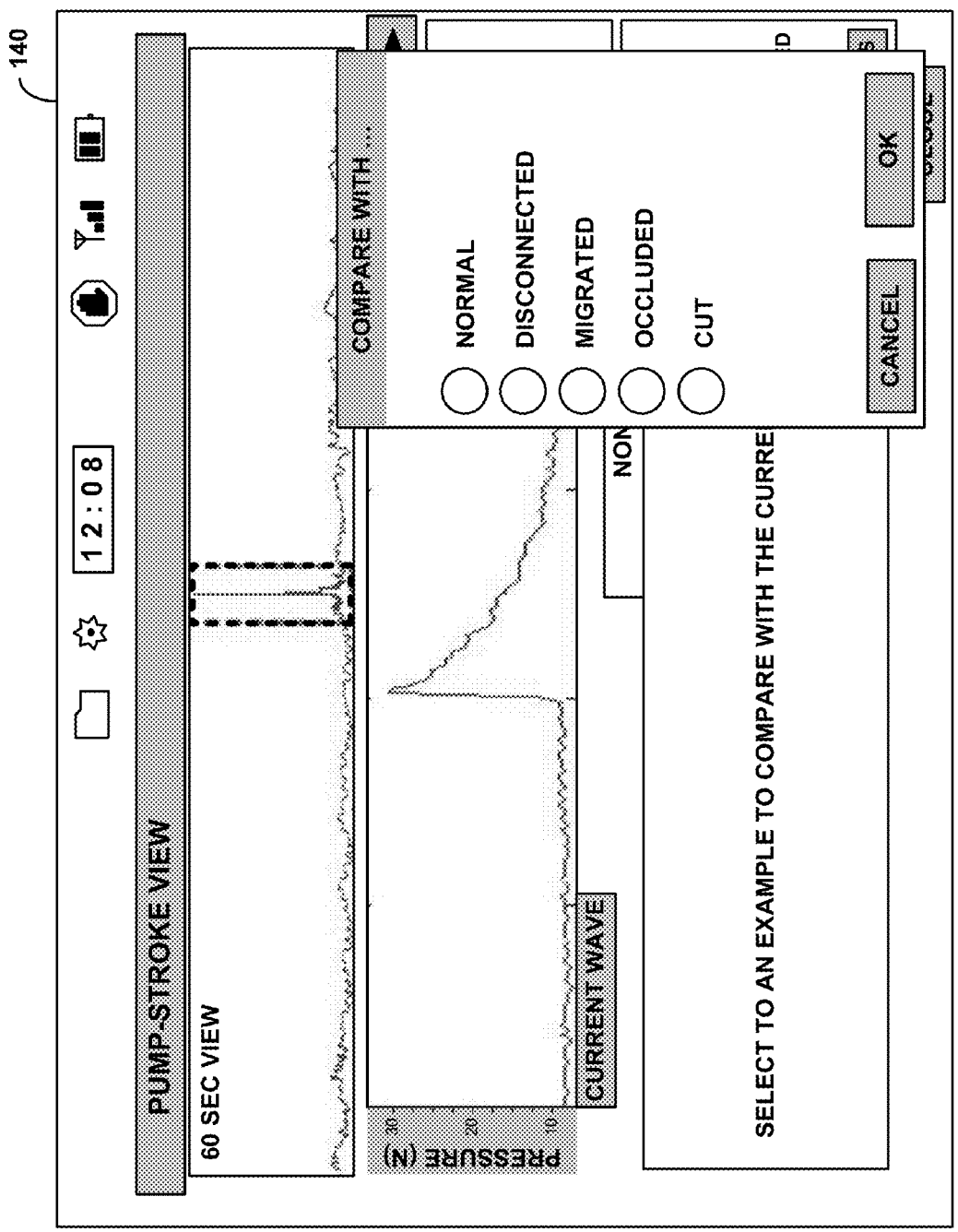
Figure 8M:
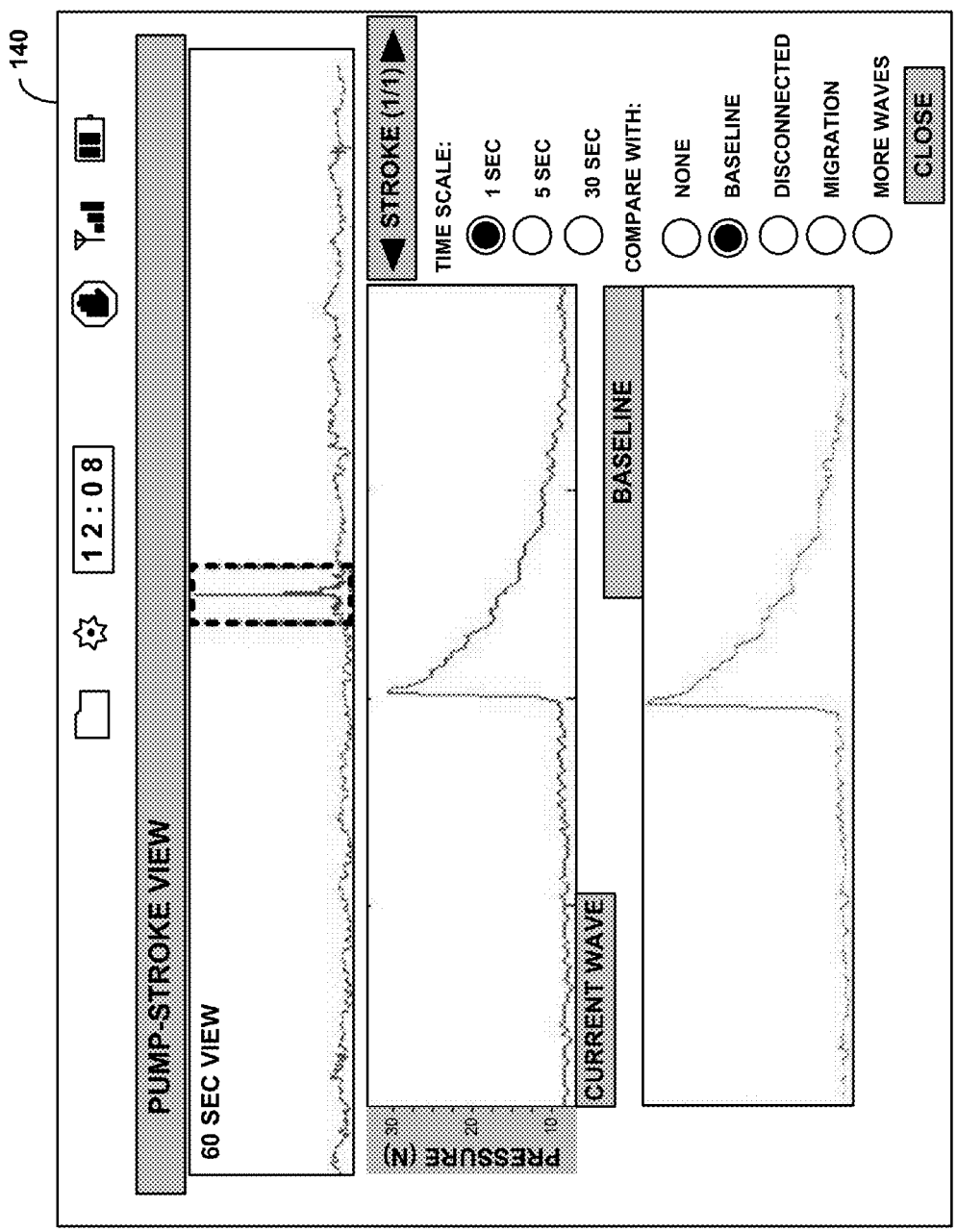
Figure 8N:
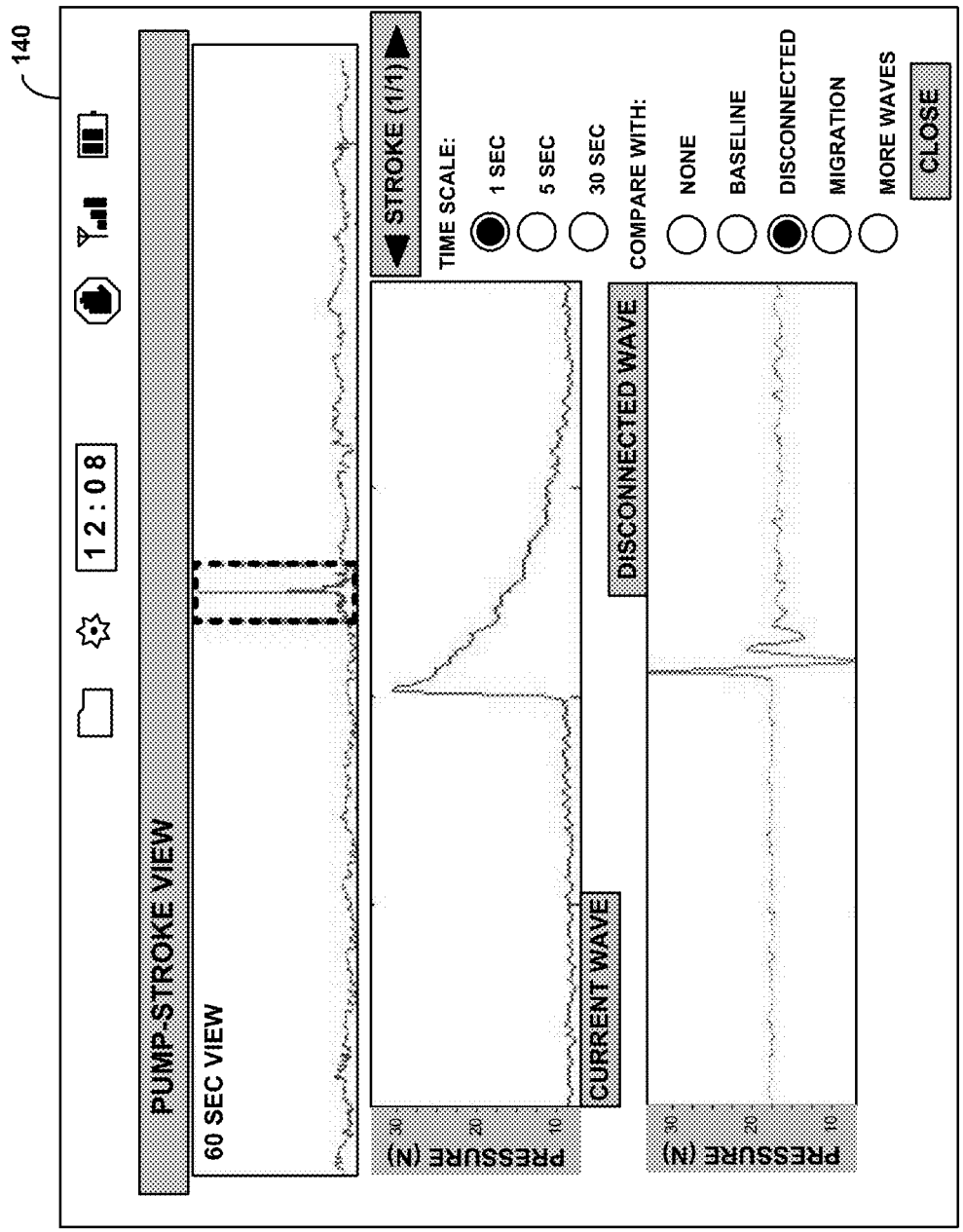
Figure 8O:
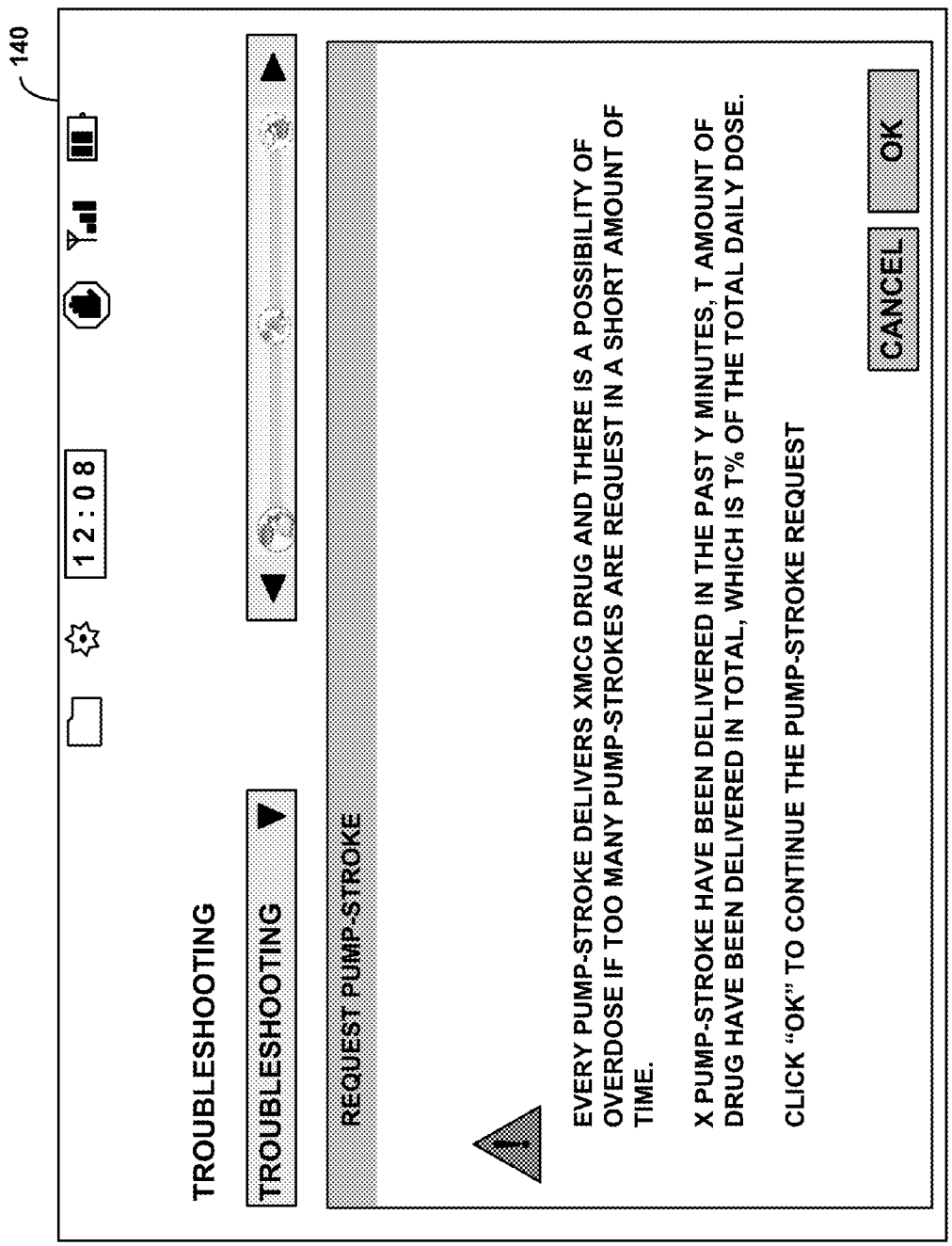

FIGS. 8A-8O are screenshots illustrating an example user interface 140 for troubleshooting using the live pressure selection. In FIG. 7, the user had selected "live pressure" under troubleshooting, which will allow the user to display a real-time catheter pressure waveform, which may be measured using pressure sensors associated with IMD 12 as described above. The user may be able to select the time span of the window of the waveform. In this example, the selected time span is 30 seconds. The spike in the waveform in the example of FIG. 8A may correspond to the delivery of the pump stroke and through the catheter, and the associated pressure measurement. The user may be prompted that to be able to view the "pump-stroke view," the live pressure waveform may be paused. The screen may also show additional information such as, for example, the next time the pump will deliver a stroke in terms of time units, for example, X minutes and Y seconds. The screen may also allow the user to make a selection to request a stroke at that moment if, for example, the time until the next pump stoke is too long and the user may not be able to wait. In one example, when the user requests a pump stoke to be delivered before the scheduled time, a count down may appear to indicate the new time remaining until the next delivery. The time until the next pump stroke delivery may be defined by the user or may be preset by the programmer, for example.

From this screen, the user may also select to pause the live pressure waveform to save the waveform. In this example, the waveform is not paused, and therefore, the "save to report" button 142 is not highlighted.

The user may select to pause the waveform, which will result in pausing the live pressure waveform at the selected time, as seen in FIG. 8B. Additionally, the "save to report" button 142 will be highlighted and the user may select it to save the waveform as it appears on the screen to a report. However, the user may want to look at a portion of the waveform more closely, and may therefore select a short time span for the waveform window, for example 10 seconds, instead of 30 seconds. FIG. 8C is an example where the user selected a 10 second window for the waveform. As FIG. 8C illustrates, the smaller window allows the user to see the shape of the spike in the pressure waveform that resulted from the pump providing a stroke or a dose to the patient. Alternatively, the user may want to see the waveform over a larger span of time to see how the waveform behaves before and after the pump provides a stroke. The user may therefore select a larger window of view, for example, 60 seconds, as illustrated in FIG. 8D. The time frames for the window from which the user may select may be different, and may be programmable by the user. Additionally, the user may have more options for window times, and the three times shown here are merely illustrative. In one example, a historical waveform, i.e., a waveform recorded X minutes ago may be recalled by the user if the waveform is out of the viewing window range, and X may be defined in the programmer.

In some examples, there may be problems with the catheter and when the pump provides a stroke, the fluid may not be deliverable. The pressure waveform may allow a user to determine the existence of such problems based on the shape and values of different portions of the waveform. In other examples, additional information may be provided to the user, for example, the pressure sensors may sense that the pressure is greater or lower than a certain threshold pressure. As a result, an alert 144 may be displayed to the user as shown in FIG. 8E, indicating that the pressure is out of range and that there may be an occlusion associated with the catheter.

The user interface may provide to the user more information regarding the warning by selecting a help button 146 next to the warning 144 as shown in FIG. 8F. In this example, the screen may indicate to the user to aspirate the cap, and if the catheter pressure is back into range, i.e., displayed on the screen, then occlusion is confirmed. Otherwise, the pressure sensor may be faulty. Other issues related to losing pressure may be associated with warning messages to display for a user on the screen and related recommendations on diagnosis may also be provided in a similar fashion.

Referring again to FIG. 8B, where the user had selected to pause the waveform, the "save to report" button had been highlighted and the user is able to save the waveform to a report for further analysis. The "save to report" button may be selected as illustrated in FIG. 8G, resulting in the screen showing an indicator 141 that the waveform is being saved. When the waveform is saved, the live pressure waveform may revert back to being displayed as shown in FIG. 8H.

In one example, when the pump had not recently provided a stroke, and the time until the next stroke may be too long for the user to wait, the user may request a pump-stroke, as illustrated in FIG. 8I. For example, in some therapy programs, a pump stroke may be provided only a few times a day, which may not be around the time the user is trying to troubleshoot the system. In other examples, the user may want to confirm a certain behavior and request several pump strokes within one session. For example, a user may be diagnosing posture-related catheter and/or pump issues, and may place the patient in different postures and request a pump stroke for each posture.

When the pump stroke is requested, the pump may provide the stroke at the amount shown next to the "here" button on the screen, e.g., "xmcg per pump-stroke." The value of the pump stroke may depend on the therapy program, or may be specified by the user. In some examples, for some therapy programs, the usual amount may not be an amount that a patient should receive more than the specified times or at the specified intervals, therefore, a clinician may change the pumped dosage amount to a more moderate level, which would not cause overdosing yet allow a user to monitor the catheter and/or pump functionality. When the pump stroke is provided, a new waveform may appear showing the pressure waveform corresponding to the pumped stroke, as shown in FIG. 8J. Again, the user may select to pause the display to be able to further analyze the resulting waveform.

In one example, the user may want to analyze the waveform to determine the pressure decay of the catheter to be able to further determine the catheter patency and the performance of the catheter and/or pump. The user may select the "pump-stroke view" button 148 to view the waveform more closely, as shown in FIG. 8K. Once the user interface screen presents the pump-stroke view, the user may be able to zoom in on portions of the waveform by selecting a box 143 around the desired portion, as shown in FIG. 8K. Selecting the desired portion may result in a second display below the waveform showing the zoomed-in portion in a window 145, labeled "current wave."

In some examples, the user may have stored more than one stroke for a specific session, and may scroll among the strokes to view their corresponding waveforms. The zoomed in waveform may also result in displaying a new time scale more appropriate for the zoomed in portion. In this example, the time scale may be 1 second, but the user may be able to select other time scales, which may zoom in or out of the centered portion. The user may also have an option to compare the selected waveform to other waveforms corresponding to other conditions. In this example, the user had not selected another waveform to which the current wave should be compared. Some examples of other waveforms to compare the current wave to may be "baseline" which may correspond to a waveform measured at a time when the catheter was known to be working reasonably well, e.g., when newly implanted or following readjustment and/or repair. Another waveform may be "disconnected" when the catheter and pump may be disconnected from the user and no fluid is delivered. Another waveform may be "migrated," which may be a waveform associated with a condition where the catheter tip may be out of, i.e., not disposed in, CSF. By comparing to waveforms associated with certain conditions of the catheter and/or pump, the user may be able to determine the current condition of the catheter and/or pump, by determining the waveform that most closely matches the current waveform.

The user may also select "more options" to see more options for waveforms to compare the current wave. The user may then be presented with more options such as those shown in the pop up window in FIG. 8L. Some examples of other waveforms may be "normal," "disconnected," "migrated," "occluded," and "cut." When one of these waveforms is selected, the corresponding waveform is displayed so that a user may compare the current waveform to the saved template waveforms to assist in determining which one may match so as to determine the condition of the catheter and/or pump for more accurate troubleshooting. In one example, the comparison may be done manually by the user by looking at both waveforms and comparing them. In another example, the comparison may be done automatically using a comparison algorithm. In some examples, the comparison may be done by calculating the decay time, i.e., the time it takes for the pressure waveform to go from the peak of the spike to the signature pressure level. In one example, decay times associated with different waveforms may be programmed into the programmer 20 and/or IMD 12, and a comparison of the decay time of the current wave with the stored decay times may be performed to determine the condition of the catheter.

In one example, as illustrated in FIG. 8M, a user may select to compare the current wave to a baseline. When the user selects the baseline wave to compare, a baseline may be displayed in a window below the current wave window and may scale it at the same level as the current wave window for easier comparison by the user. The windows may also be automatically aligned as to show the waveforms at the same portion of the waveform. In this example, the two waves may look similar in the portion showing the pressure decay, and may indicate that there may be a close match between the current waveform and the baseline waveform, thus indicating that there are no issues with the catheter and/or pump as they may be functioning as expected compared to the baseline waveform. In one example, the user may select a baseline from a list of historical baselines and/or baselines at different postures.

The user may select other waveforms to compare the current wave to so as to ensure that there is not a match with other abnormal conditions. For example, as illustrated in FIG. 8N, the user may select to display the waveform for a disconnected catheter to compare with the current waveform. The waveform for the disconnected condition may be shown in the window below the current wave window. In one example, one window may be displayed, and the waveforms may be overlaid on top of each other. As illustrated, the current wave may not look anything like the waveform of a disconnected catheter, and therefore, the user may conclude that the catheter is not disconnected. Therefore, the user may be able to eliminate catheter issues by comparing the current wave to the waveforms associated with certain faulty conditions.

Referring back to FIG. 8I, the user may select the button to request pump-stroke to be delivered to acquire pressure decay information and waveform. As mentioned above, there may be issues associated with requesting a pump-stroke outside the scheduled doses. The user may be presented with an alert regarding the requested pump-stroke as illustrated in FIG. 8O. The alert may be provided to remind the user to be cautious when applying therapy outside of the programmed therapy. In this example, the alert may indicate to the user the dosage provided for every pump-stroke and that overdosing may occur if the pump-stroke functionality is requested too many times in a short time frame. Additionally, the alert may indicate to the user the amount already delivered to the patient in a certain time frame, and the percentage of the daily dose already delivered. The percentage may be also determined with respect to weekly or monthly time frames, for example. The alert allows the user to make a determination based on the presented information as to whether to continue with the requested pump-stroke or not. If the user clicks "OK," the requested pump-stroke is delivered to the patient. Otherwise, the user may click "cancel" if the user determines, based on the presented information, that overdosing may occur if the requested pump-stroke is delivered.

FIGS. 9A-9G are screenshots illustrating an example user interface 150 for troubleshooting using pressure snapshot/baseline. Referring back to FIG. 7, the user may select "pressure snapshot/baseline" under troubleshooting, which may allow the user to record catheter pressure waveform for later comparison, i.e., establish a baseline pressure decay profile to be used in subsequent sessions for comparison with subsequent measurements of pressure in the catheter. The user may perform this when the user knows that the catheter and/or pump may be functioning correctly or working well, e.g., at the time of implant. Subsequent pressure measurements may be compared to the baseline pressure by comparing the decay profile of the measured pressure with the decay profile of the baseline pressure. In one example, the maximum values of the measured pressure and the baseline pressure, i.e., at the spike after a pump stroke is delivered may be compared. In another example, the decay time of the measured pressure and the decay time of the baseline pressure may be compared, where, for example, a longer decay time in the measured pressure may indicate occlusion in the catheter.

In some examples, the user may be prompted to capture a baseline pressure decay profile. In another example, the system may be setup to automatically capture a baseline pressure decay profile periodically or when a certain event occurs, e.g., replacing the catheter, adjusting the dose, or reconfiguring the IMD. In some examples, automatic capturing of a baseline decay profile may occur when a dose is delivered, and the frequency of the automatic capture may be set to default times (e.g., day, time of day, or day of week) or may be selected by the user. In other examples, the user may be alerted to capture a baseline pressure decay profile if a baseline pressure decay profile has not yet been saved for the particular user and/or the catheter attached to the IMD.

Figure 9A:
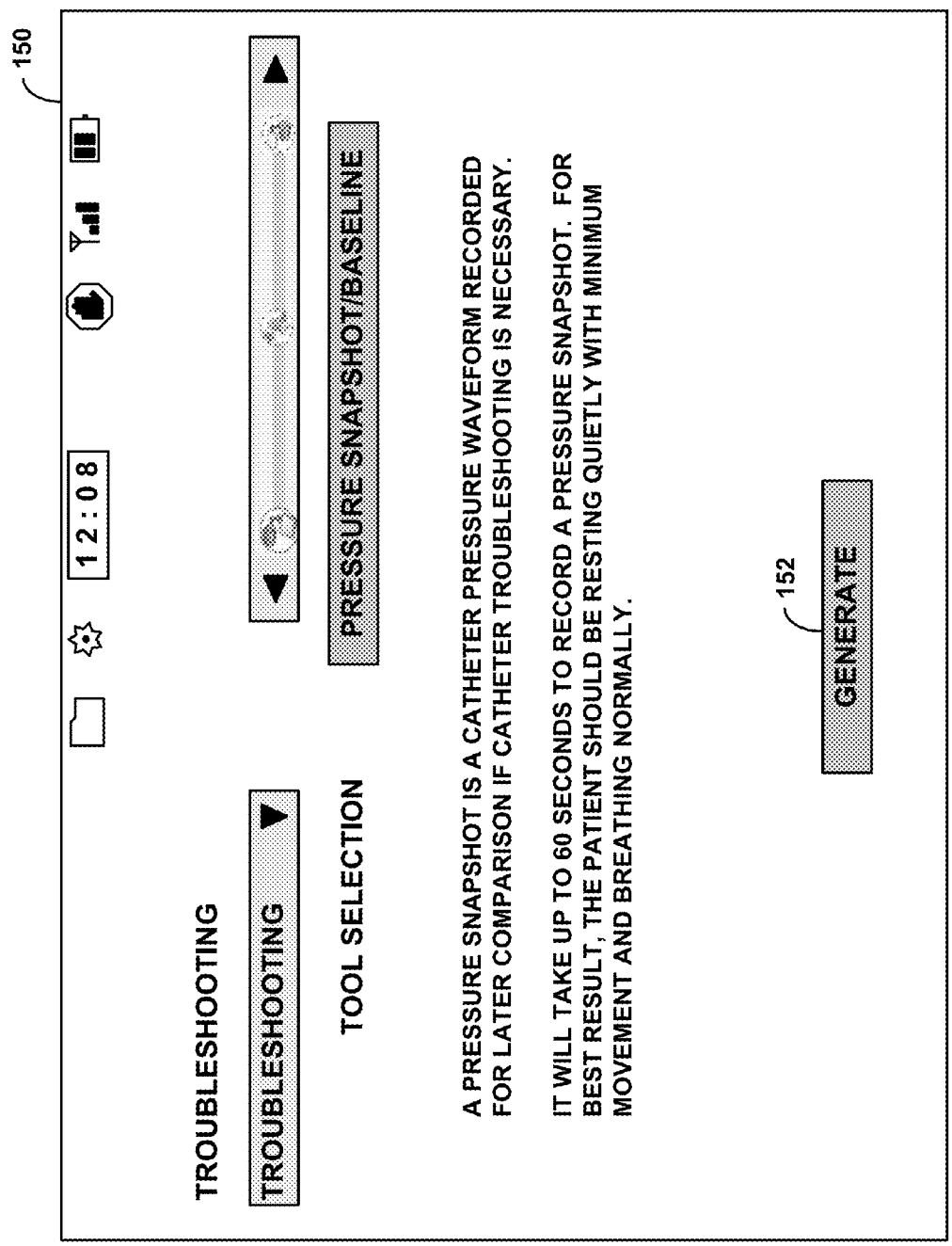
FIGS. 9A-9G are screenshots illustrating an example user interface for troubleshooting using a pressure snapshot/baseline.
Figure 9B:
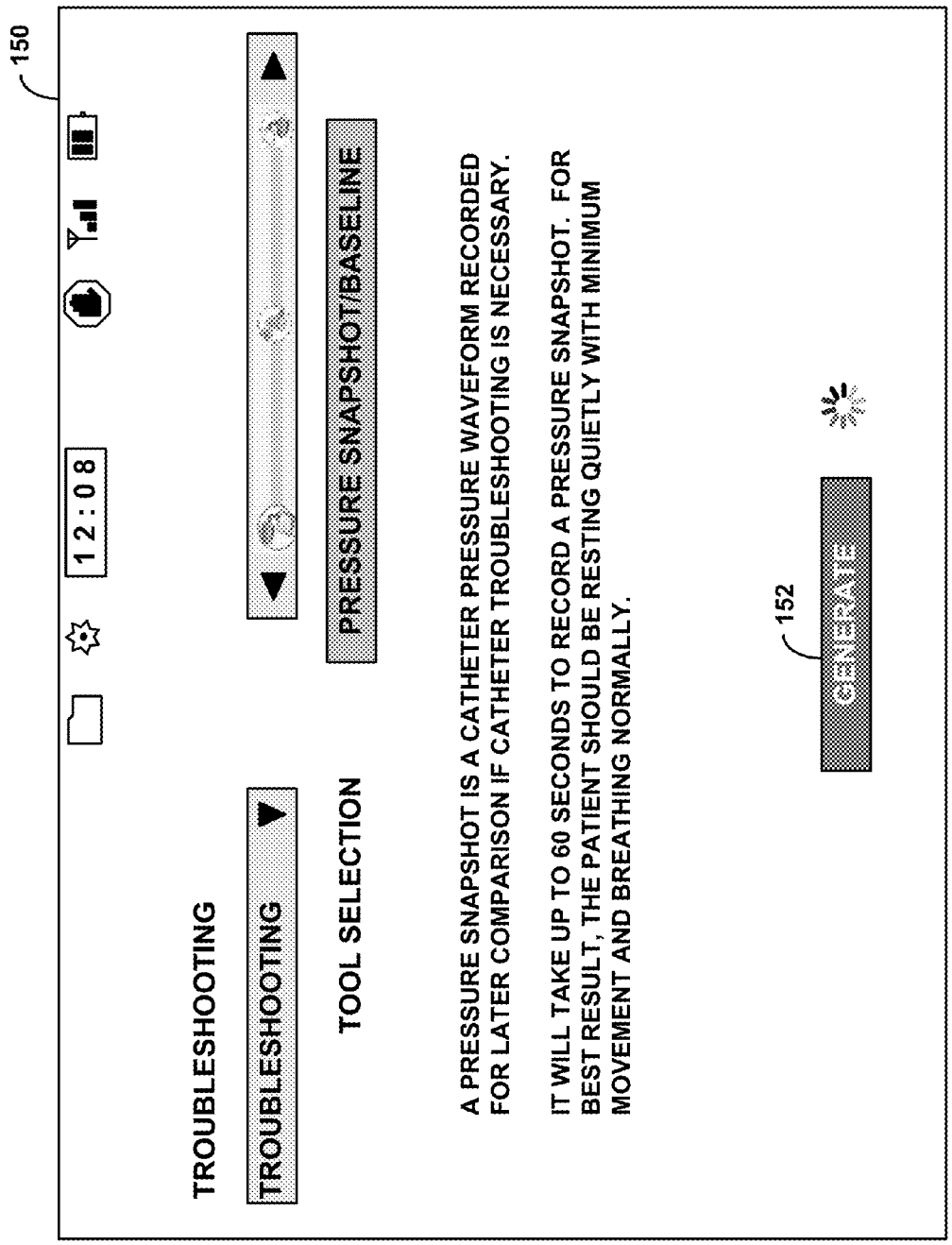

As FIG. 9A illustrates that, after the user had selected "pressure snapshot/baseline" and clicked "OK," the user interface may display information for the user regarding the function. The user interface may also display instructions as how to best obtain the best results. In this example, the instructions indicate that the patient should be resting quietly with minimum movement and breathing normally for at least 60 seconds to obtain the desirable pressure snapshot. The user may then select the "generate" button 152 to begin generating the requested pressure snapshot/baseline waveform. Once selected, the "generate" button 152 may be grayed out and an indicator that the waveform is being generated may be displayed as illustrated in FIG. 9B.

Figure 9C:
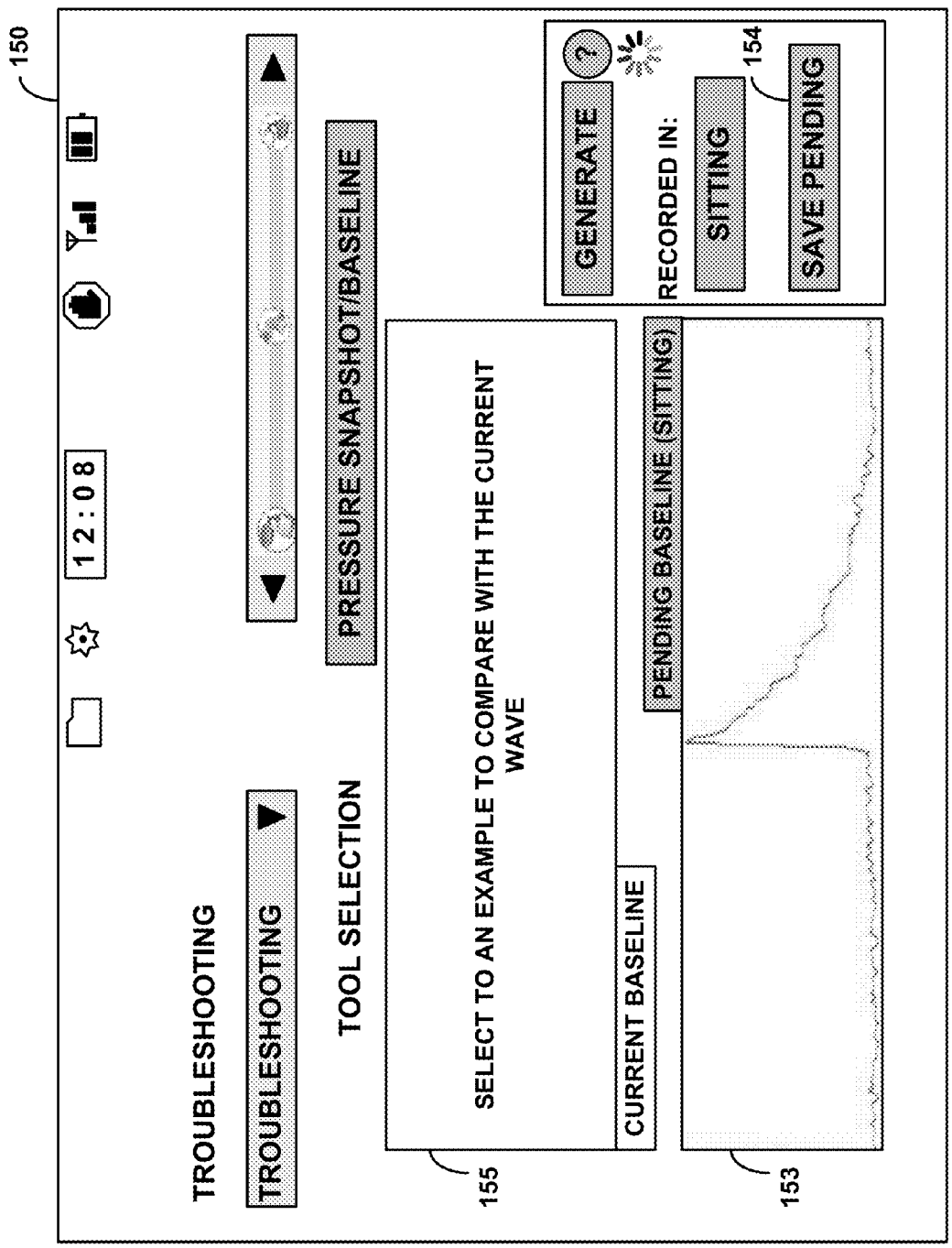

FIG. 9C illustrates the display of the user interface once the requested pressure snapshot/waveform has been obtained. The waveform may be displayed in the lower window 153, labeled "pending baseline (sitting)," which may indicate that a baseline has been obtained and the associated posture, if applicable. The first time the user obtains a pressure snapshot/baseline, there may be no existing baseline, and therefore, as illustrated in FIG. 9C, the top window 155, labeled "current baseline" may be blank and may indicate to the user that there is no current baseline, and that to establish one, the pending baseline needs to be saved as the baseline to become the current baseline. In some examples, the waveforms associated with a catheter may vary depending on the posture of the patient when therapy is delivered. In this example, the pressure snapshot/baseline may be obtained while the patient is sitting, and the user may be able to indicate that the waveform corresponds to a sitting position. The user may be able to record a baseline for several possible postures, e.g., sitting, sleeping, walking, and the like. In some examples, a baseline may be saved for each posture, and when comparing later for troubleshooting purposes, the baseline for the patient's posture when a measurement is made may be used for comparison.

Figure 9D:
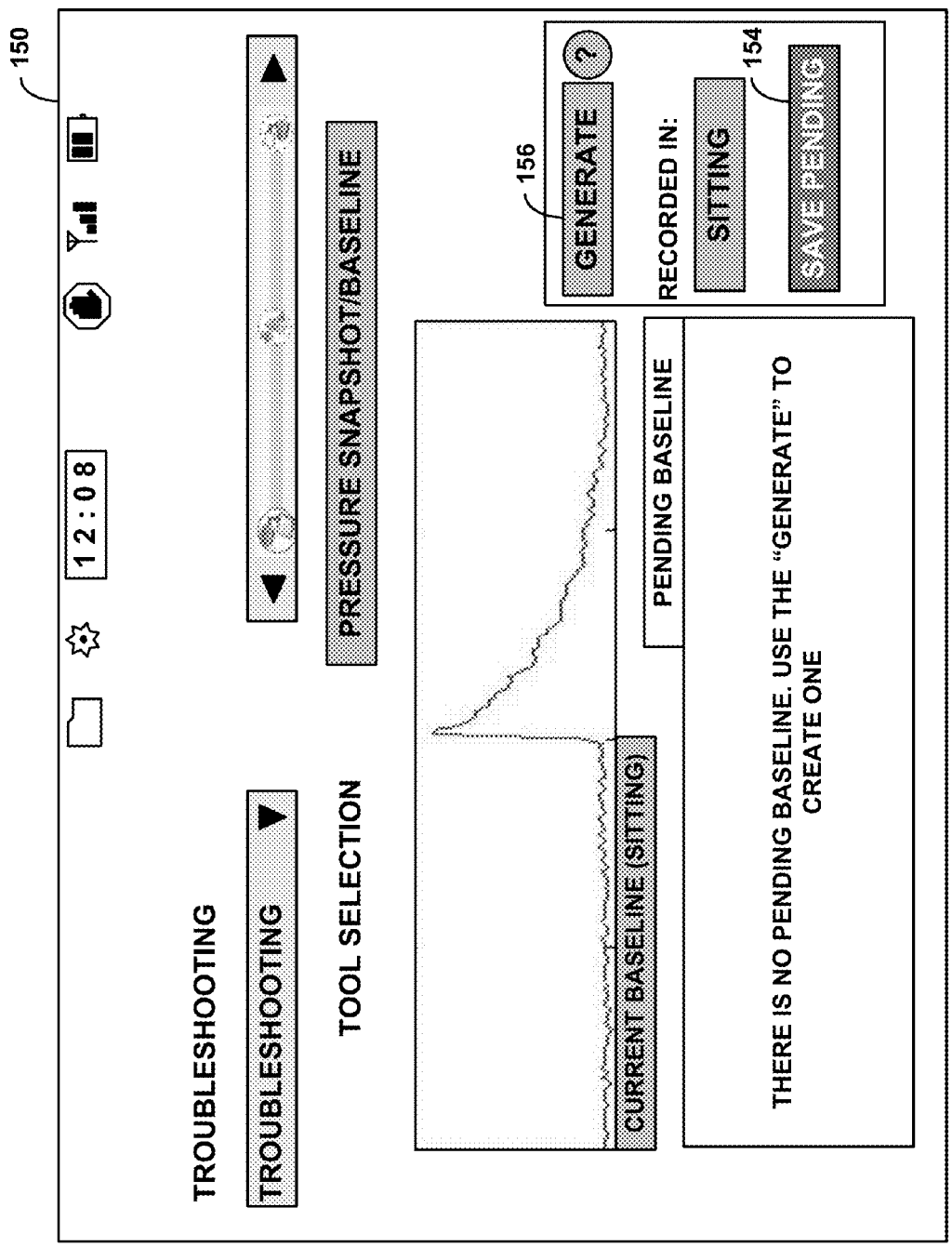

Once the user is satisfied with the pending baseline, the user may select the "save pending" button 154, as illustrated in FIG. 9D. As a result, the pending baseline waveform may become the current baseline. In this example, the current baseline may be associated with the sitting position to show the baseline of the pressure decay of the catheter when the patient is sitting. When the current baseline is saved, the pending baseline window becomes blank, and the display indicates to the user that there is no pending baseline. If the user wants to obtain a new baseline, the user may select the "generate" button 156 to create a new baseline.

Figure 9E:
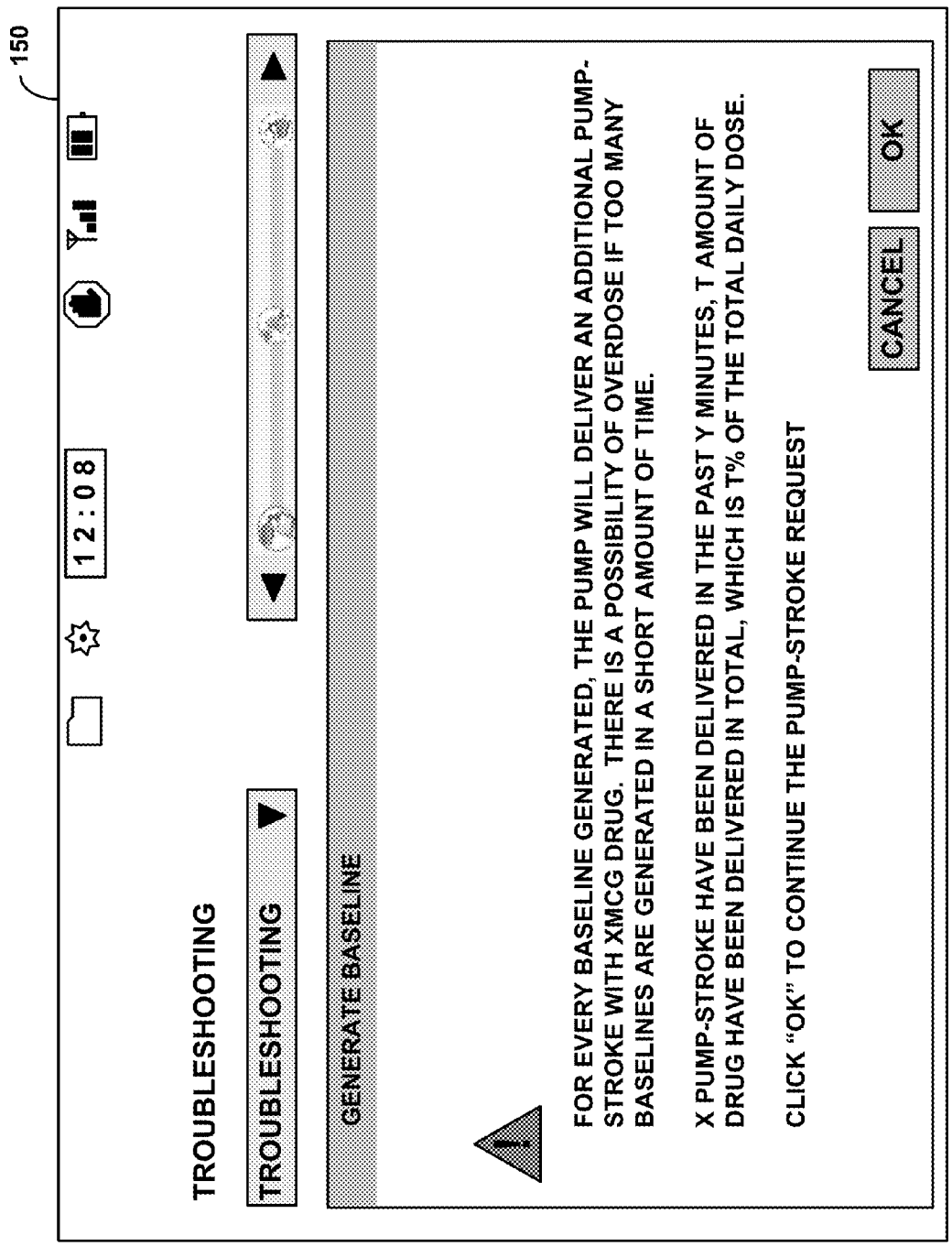

When the user selects to generate a new baseline, the display may present an alert to the user as illustrated in FIG. 9E. When a new baseline is generated, the pump delivers a dose of the drug to the patient, and therefore, overdose is still an issue if too many pump-strokes are delivered. Therefore, the user may be alerted as to the drug amount already delivered to the patient, assisting the user in determining to make a decision as to whether to deliver any more doses to obtain a baseline. If the user decides against obtaining another baseline at the current session to avoid overdosing issues, the user may select the "cancel" button, otherwise, the user may select "OK" to obtain another baseline.

Figure 9F:
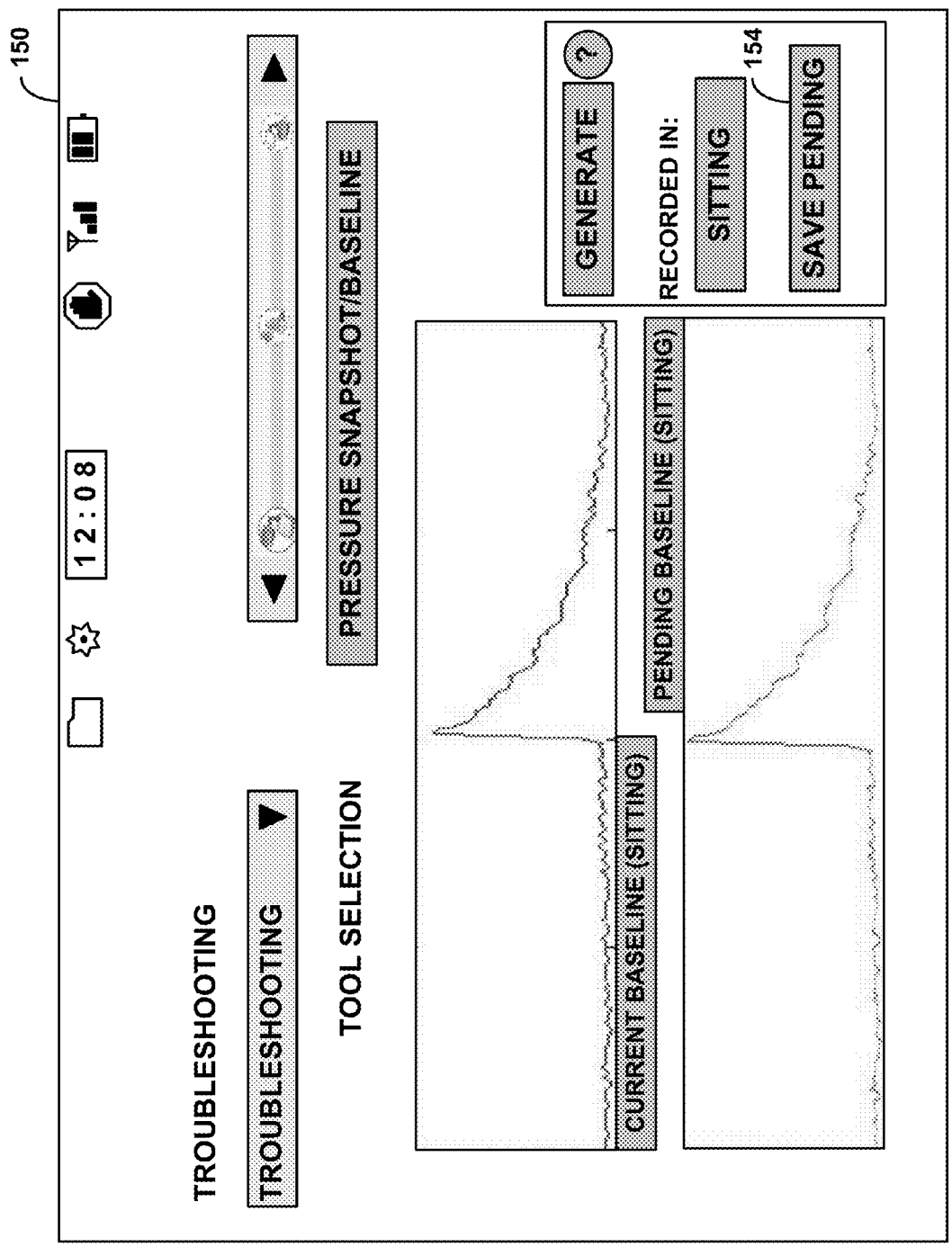
Figure 9G:
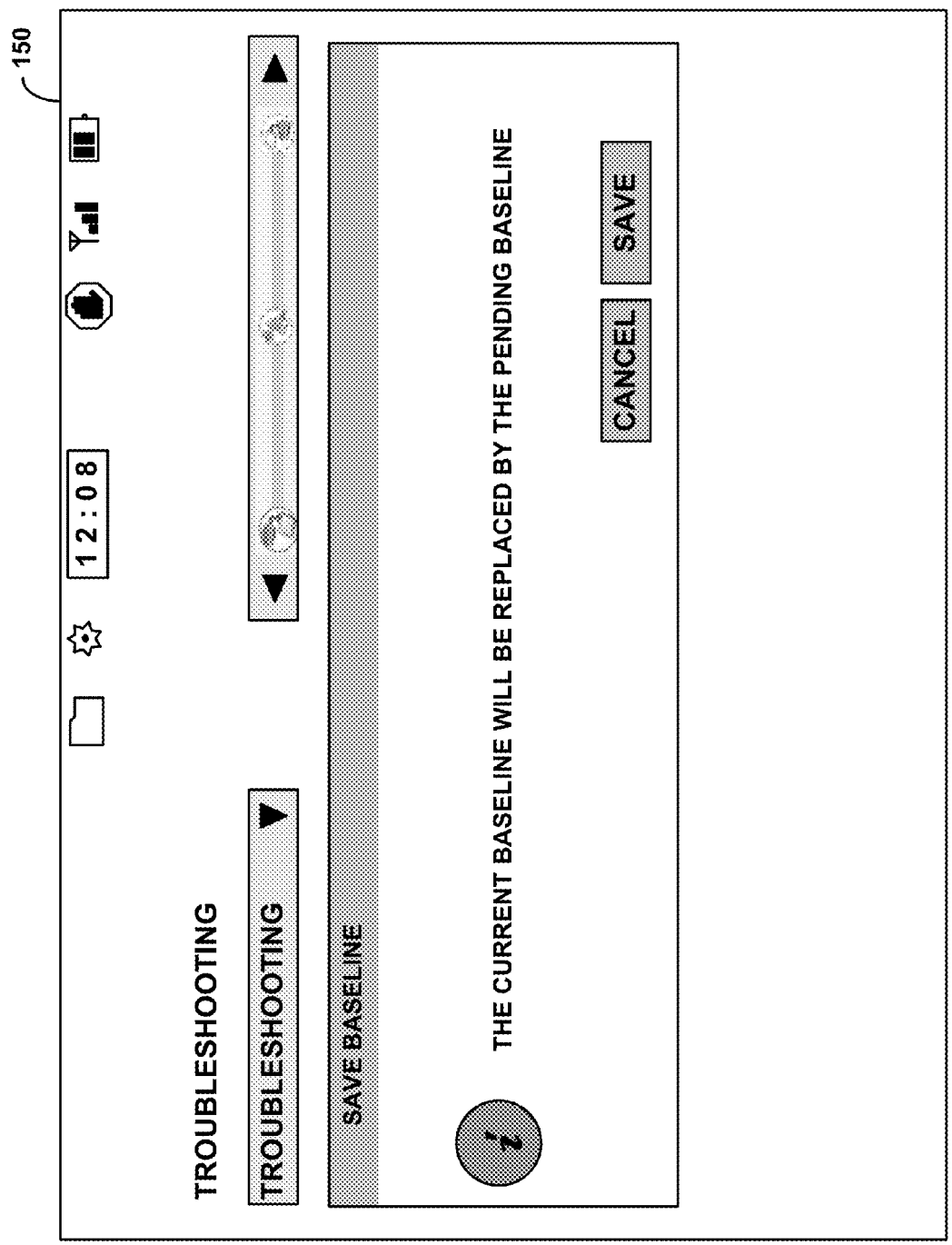

In an example, the user may choose to obtain another baseline, and as in FIG. 9C, a new baseline waveform is obtained and displayed as the new pending baseline, as illustrated in FIG. 9F. In this example, the baseline previously obtained may be displayed as the current baseline, and the new pending baseline may be displayed in the pending baseline window. The user may select to use the pending baseline as the current one by selecting the "save pending" button 154. The user will then be presented with an alert, as illustrated in FIG. 9G, indicating that by selecting to save the pending baseline, the current baseline will be replaced by the pending baseline. The user may select "cancel" if the current baseline is not to be replaced, otherwise, the user may select "save" to use the pending baseline as the current one and to replace it. In an example, the user may be able to save previous baselines before saving a pending one as the current baseline to create a historical log of baselines. Therefore, the most recently-obtained baseline may be saved as the current baseline, and previously-obtained baselines may be saved according to the dates they were obtained, for example. In this manner, the user may be able to retrieve previous baselines for comparison and/or analysis.

Figure 10A:
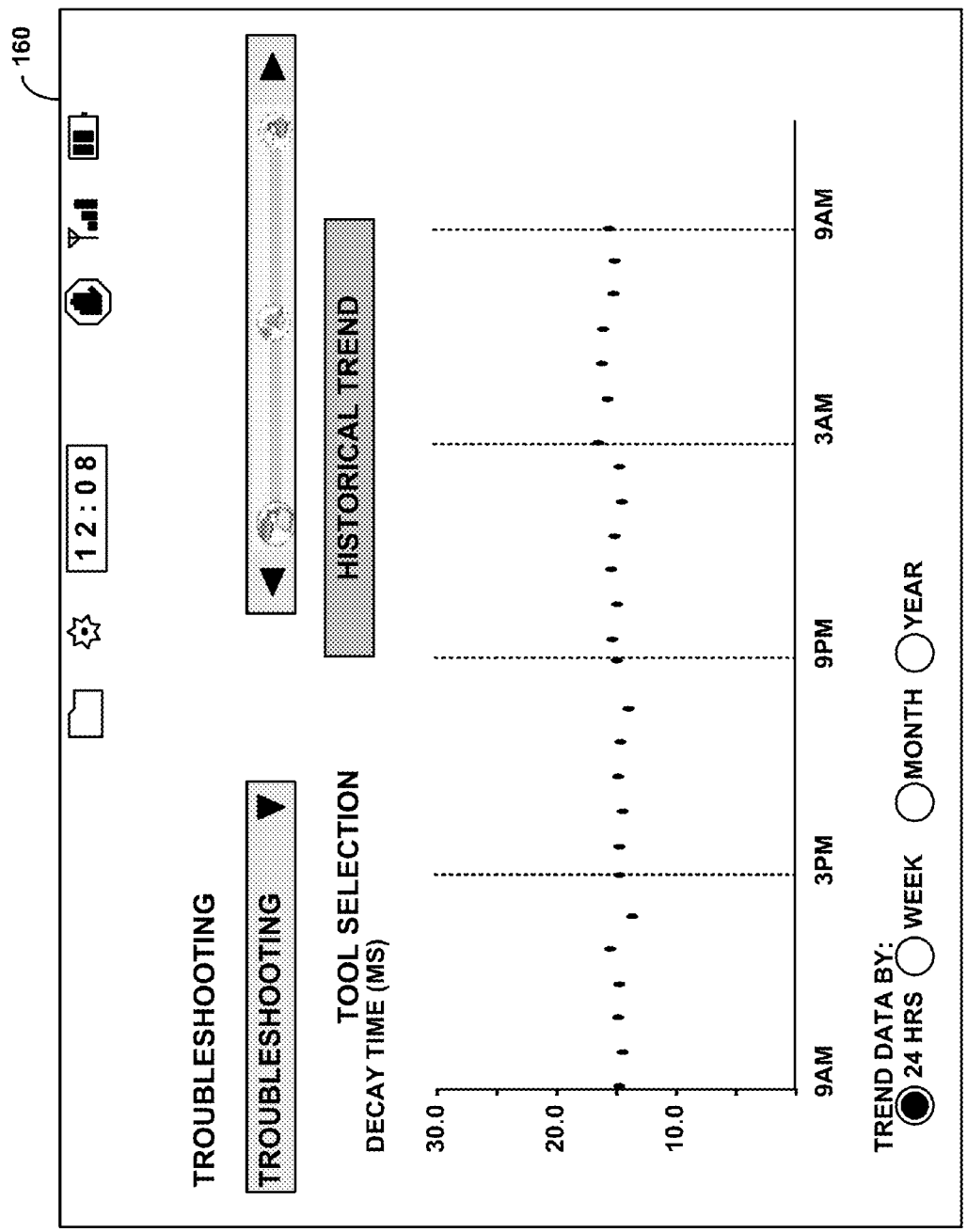
FIGS. 10A-10D are screenshots illustrating an example user interface for troubleshooting using a historical trend.
Figure 10B:
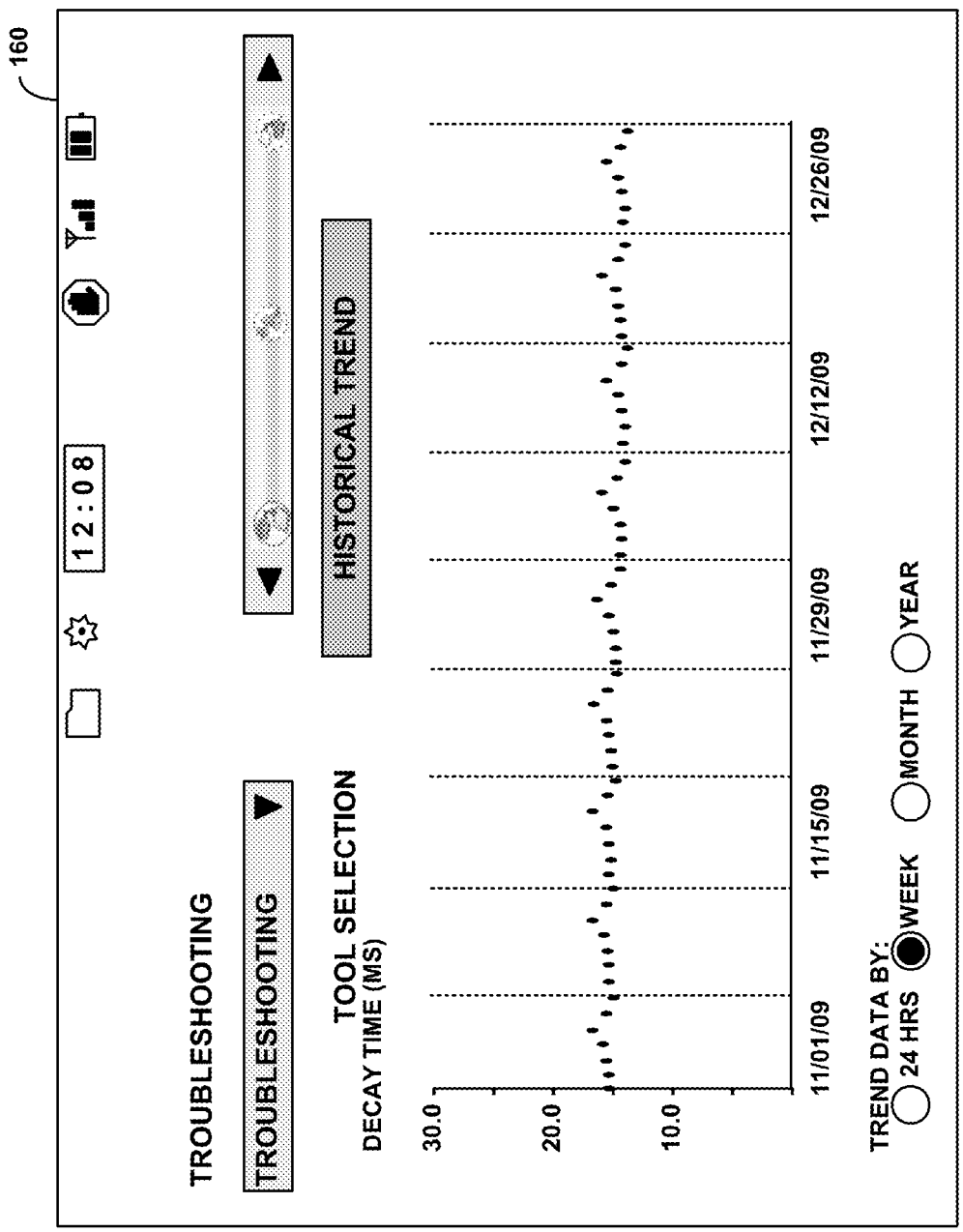
Figure 10C:
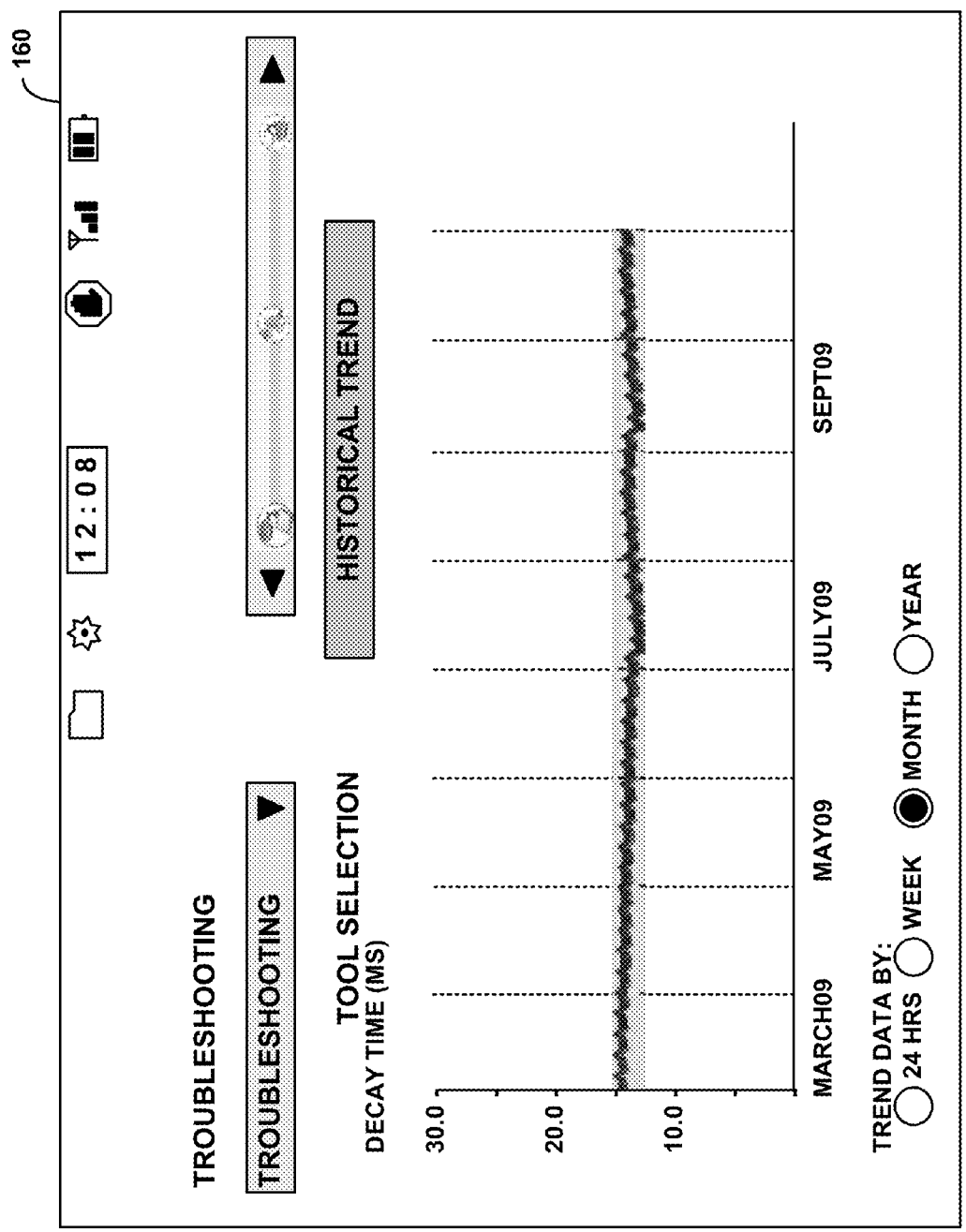
Figure 10D:
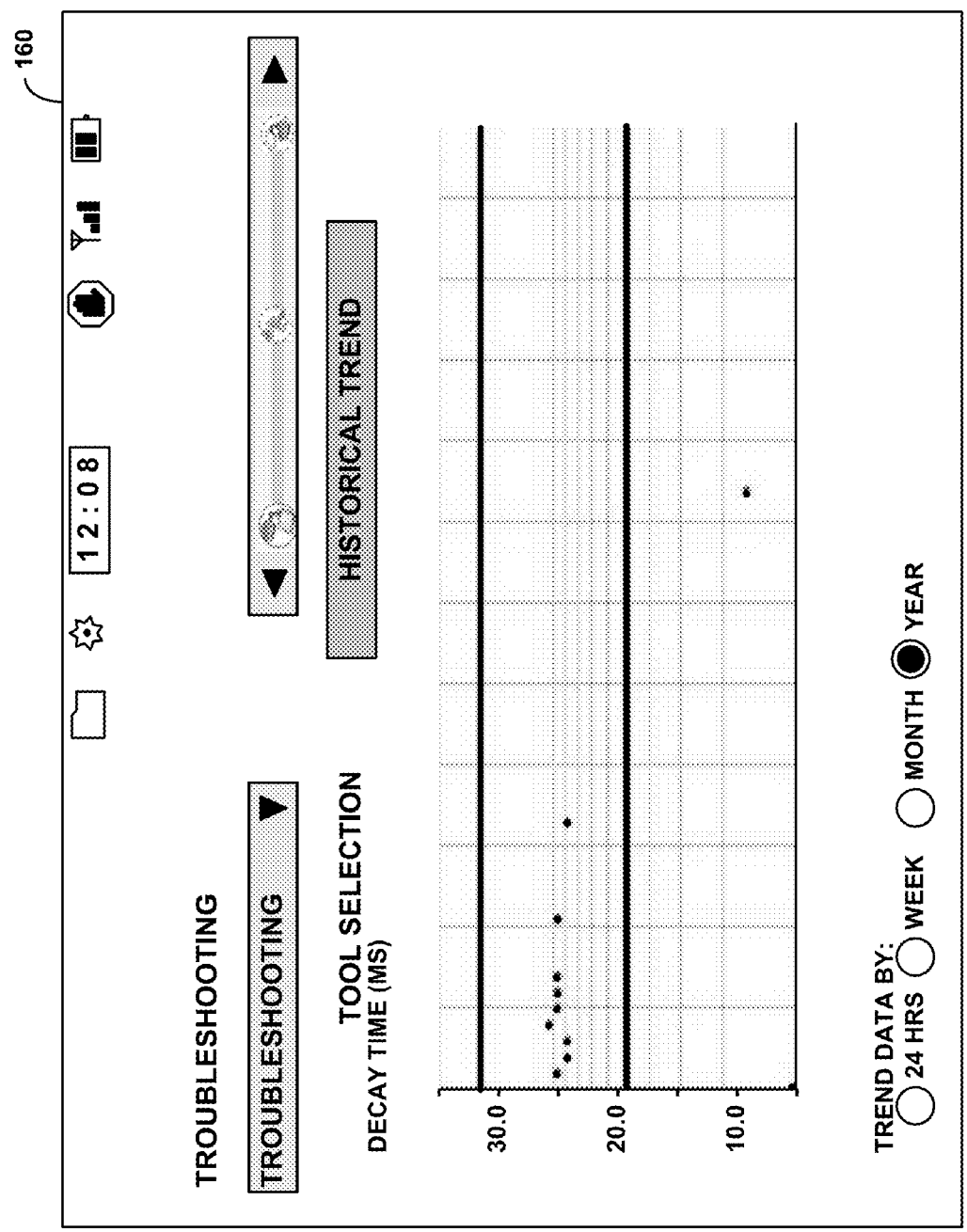

FIGS. 10A-10D are screenshots illustrating an example user interface 160 for troubleshooting using a historical trend. Referring to FIG. 7, the user may select "historical trend" under troubleshooting, which may allow the user to see a display of catheter flow resistance historical trend. The historical trend data may reflect the value of the decay time of a catheter pressure waveform over a period of time selected by the user. For example, FIG. 10A illustrates the plot of the decay times over a period of 24 hours. Each of the data points may correspond to a decay time associated with catheter pressure waveform every time the pump delivered a dosage of the drug. In one example, the decay time may not be calculated every time, but may be obtained at intervals indicated by the user. The user may also select to view the historical trend over other periods. For example, the trend may be plotted over a week's period as illustrated in FIG. 10B, over a month's period as illustrated in FIG. 10C, or over a year's period as illustrated in FIG. 10D, for example, where each of the divisions on the plot correspond to the selected range.

Other lengths of time may be used to view the plot of the decay time historical trend, and may be specified by the user. The user may analyze the historical trend of the decay time to evaluate the performance of the catheter and/or pump. In one example, the user may indicate a threshold for the decay time, and if the decay time starts approaching the threshold, an alert may be displayed for the user. In another example, the threshold may be displayed on the plot of the historical trend to show the relationship between the decay time and the threshold, as shown in FIG. 10D for example, where thresholds may be indicated with the horizontal lines. Additionally, if the decay time starts sloping towards the threshold, the user may decide not to wait until the catheter is completely faulty to change it, repair it, or adjust it, as a sloping of the historical trend may indicate, for example, that the catheter is slowly occluding.

Figure 11:
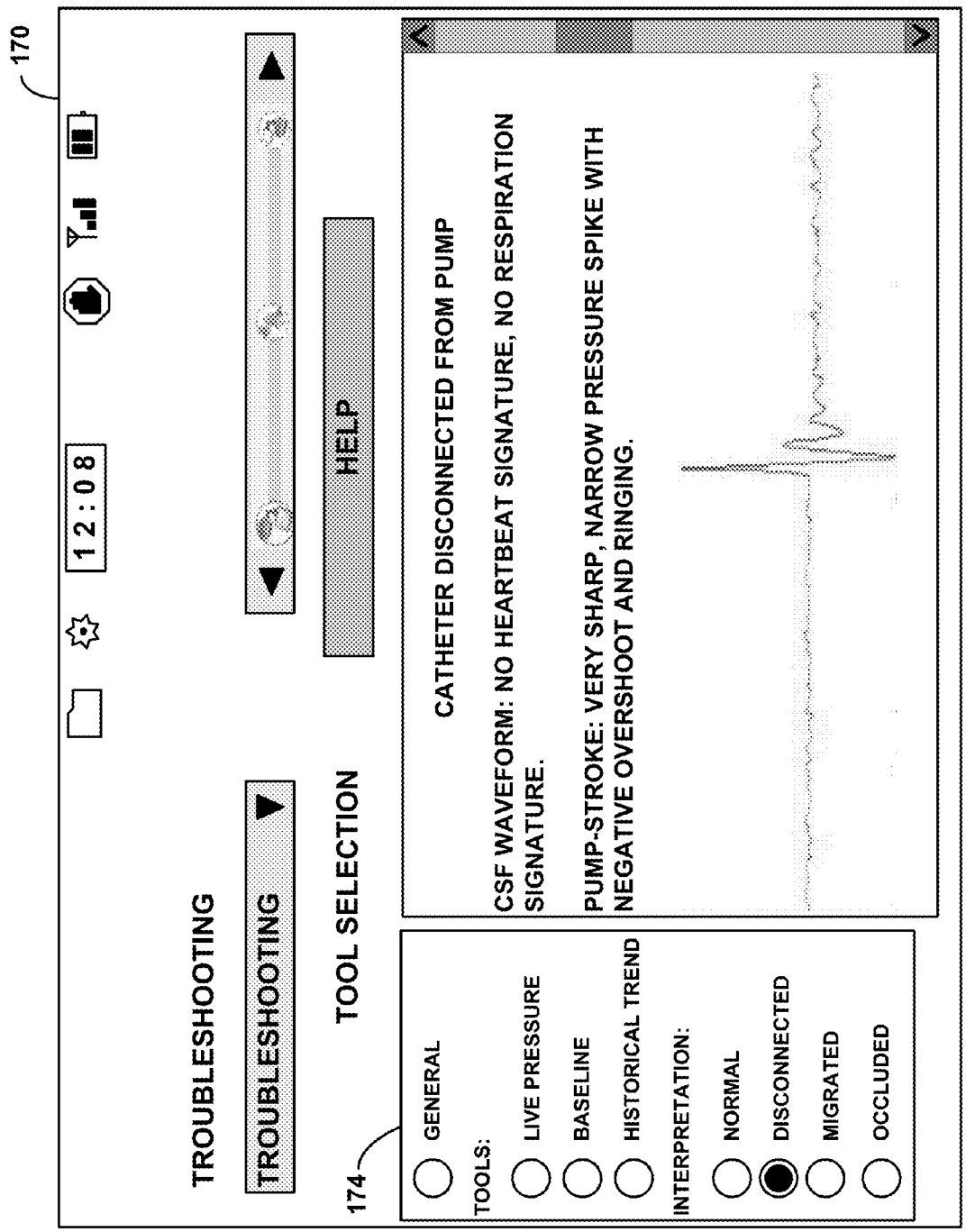
FIG. 11 is a screenshot illustrating an example user interface for a help option under troubleshooting.

FIG. 11 is a screenshot illustrating an example user interface 170 for a help option under troubleshooting. Referring to FIG. 7, the user may select "help" under troubleshooting, which may provide guidance to the user in using the troubleshooting feature. The help option may also provide example waveforms to the user to be able to identify issues with the catheter when waveforms are obtained. As FIG. 11 illustrates, the help menu may give the user options for help topics as shown on the left in box 174. Some of the help options from which the user may select are "general," "tools: live pressure," "tools: baseline," "tools: historical trend," "interpretation: normal," "interpretation: disconnected," "interpretation: migrated," and "interpretation: occluded," for example. In the example of FIG. 11, the user selected help with interpretation of disconnected. In this example, a waveform for a disconnected catheter may be displayed and an explanation may be provided as to what information the waveform may provide. In this example, a disconnected waveform may indicate a CSF waveform may result in no heartbeat signature and no respiration signature, and a pump-stroke may result in a very sharp and narrow pressure spike with negative overshoot and ringing.

Figure 12:
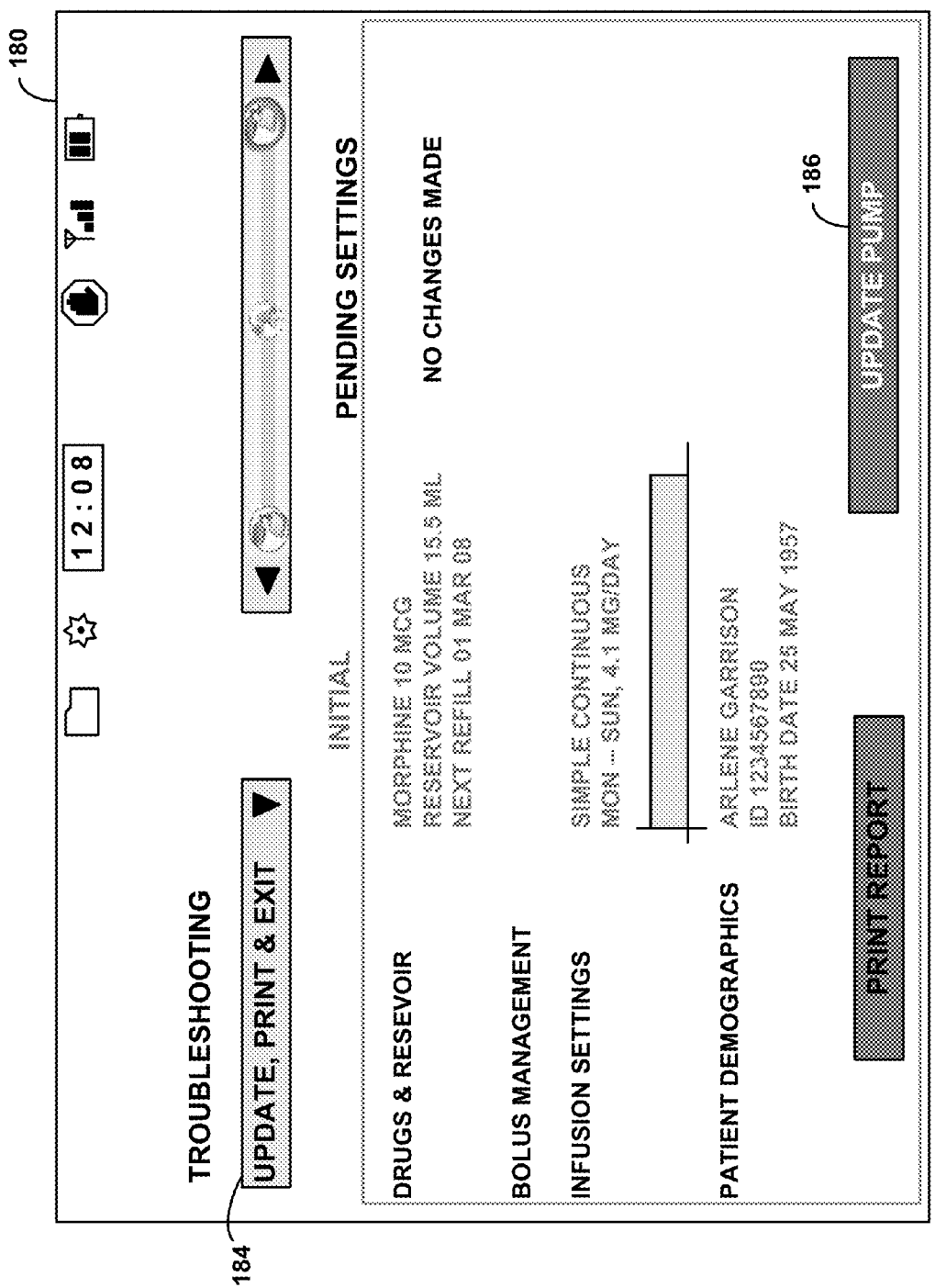
FIG. 12 is a screenshot illustrating an example user interface for updating pump information at the end of a troubleshooting session.

FIG. 12 is a screenshot illustrating an example user interface 180 for updating pump information at the end of a troubleshooting session. After performing the functions that the user may need to perform to troubleshoot the catheter and/or the pump, the user may select to "update, print & exit" under the drop down menu 184. A summary of the changes is displayed to the user in two columns showing the initial settings when the user started the current session and the pending settings as the user had modified them. If no changes were made, an indication may be made to alert the user that no changes were made during the current session. In this example, the user had not made any changes to the drugs and reservoir, the bolus management, the infusion settings, or the patient demographics. If the user had made any changes, the new changed information may be displayed in the pending settings column. The user may then review the changes and select "update pump" button 186 if satisfied. In this example, the user made no changes, and therefore, "update pump" button 186 may be grayed out and unselectable. The user may be able to print the report of the settings of the pump, whether changes were made or not.

Figure 13:
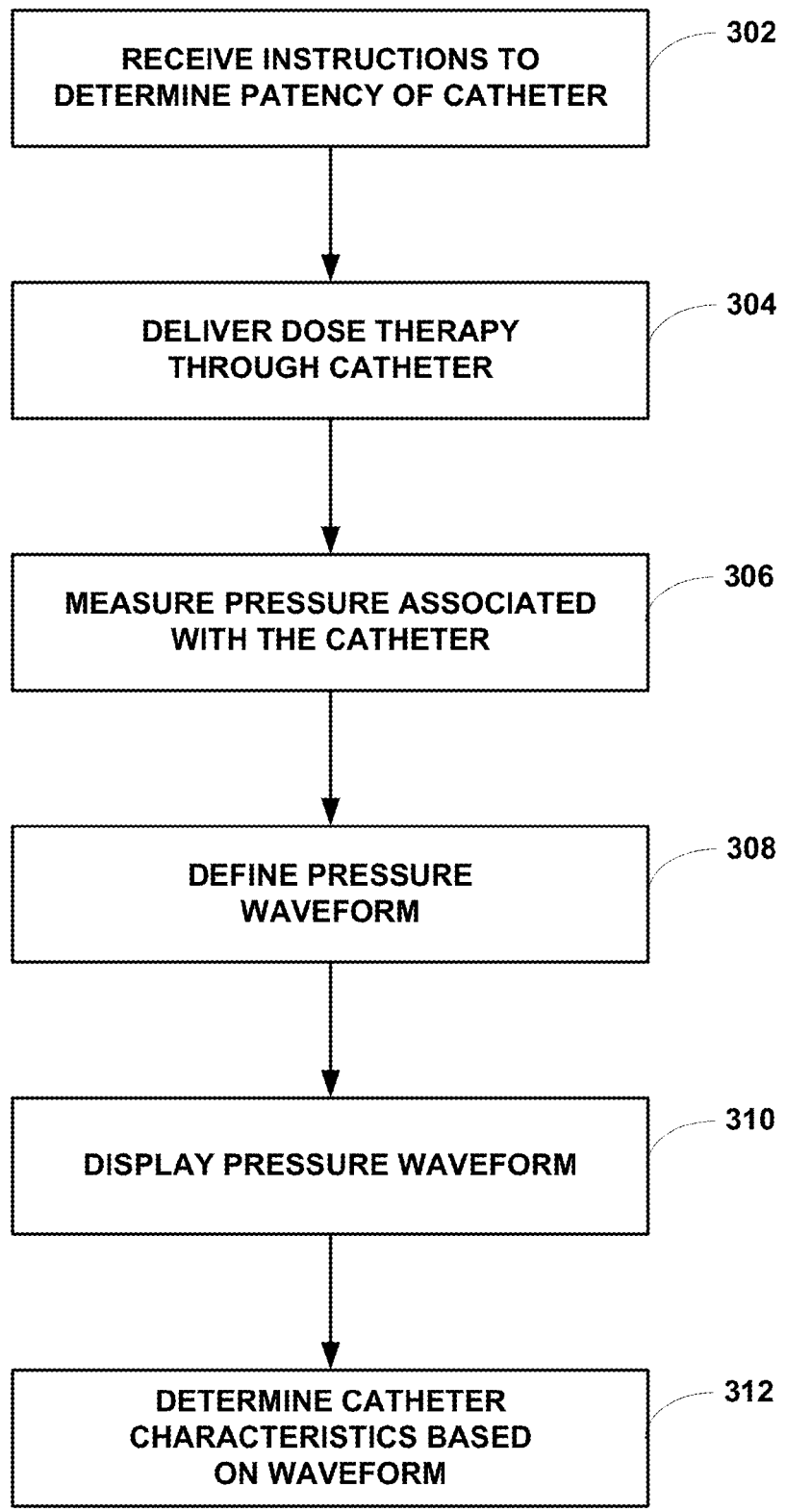
FIG. 13 is a flow diagram illustrating example operation of an implantable fluid delivery system in accordance with this disclosure.

FIG. 13 is a flow diagram illustrating example operation of an implantable medical fluid delivery system in accordance with this disclosure. A programmer, e.g., programmer 20, receives user input via the user interface 82 with instructions to determine patency of a catheter associated with implantable medical fluid deliver device 12 (302). Programmer 20 may communicate the instructions via telemetry module 88 with the implantable device 12 through telemetry module 30. In some examples, the instruction to determine of patency of a catheter may be automatic, and may be performed periodically by processor 26 of implantable device 12.

Processor 26 may provide instructions to fluid delivery pump 32 to deliver an amount of therapeutic fluid through catheter 18 to the patient. Fluid delivery pump 32 may deliver the therapeutic fluid through catheter 18 (304). Processor 26 may instruct pressure sensor 40 to measure a pressure associated with catheter 18 before, after, and during delivery of the therapeutic fluid (306). The pressure associated with the catheter may be a pressure in the catheter, or in any element in communication (e.g., fluid communication) with the catheter, such as any conduit in communication with the catheter and/or the pump through which the pump 32 delivers a therapeutic agent, e.g., internal tubing 38. In one example, a posture sensor, e.g., posture sensor 46, may determine a posture associated with the patient during delivery of the fluid and measurement of the pressure associated with the catheter.

The measured pressure may be then processed to determine or define an associated pressure waveform (308), as described above. In one example, processor 26 of implantable device 12 may process the measured pressure. In another example, the measured pressure may be communicated to programmer 20, where processor 84 may process the measured pressure. In another example, the measured pressure may be communicated to another device equipped with a processor capable of processing the measured pressure in accordance with this disclosure. The processor (e.g., processor 26 or processor 84) may define the pressure waveform associated with the catheter based on the measured pressure. The pressure waveform associated with the catheter may be the waveform of the measured pressure in response to the pump stroke of fluid delivered by the pump. In one example, the processor may define the pressure waveform associated with the catheter based on the maximum pressure level, the calculated decay time associated with the measured pressure (e.g., the amount of time required for the pulse to fall from the maximum pressure level to the signature pressure level), and/or the duration of the portion where the pressure is above a baseline pressure level (e.g., the signature pressure level). The portion where the pressure is above the baseline pressure level may be the portion corresponding to the initial rise in the pressure in response to the pump stroke delivery and until the pressure level decays back to the signature pressure level.

The processor may then cause the determined pressure waveform to be displayed on a user interface, e.g., user interface 82, (310). The catheter characteristics may then be determined based on the waveform (312). In one example, a user may determine the catheter characteristics by comparing the displayed waveform to a previously-acquired baseline waveform, e.g., a waveform acquired when the catheter was functioning properly, or waveforms associated with different catheter malfunctions. In one example, the user may determine the catheter characteristics by comparing the current waveform to a baseline waveform previously acquired and associated with the same posture as the current waveform. In one example, the processor may determine the catheter characteristic by comparing (e.g., using a comparison algorithm) the determined pressure waveform to a previously-acquired baseline waveform. In this example, it may not be necessary to display the waveform for comparison purposes, as the processor makes the determination based on the waveform.

In another example, the user and/or processor may determine the catheter characteristics based on a pressure decay time, e.g., the time required for the measured pressure to fall from a maximum pressure to the baseline pressure level. In this example, the pressure decay time of the current waveform may be compared to pressure decay times associated with other waveforms, e.g., waveforms associated with a catheter functioning properly, or waveforms associated with a catheter with different malfunctions (e.g., disconnected, occluded, migrated, or cut). Additionally, the decay time of the current waveform may be compared to pressure decay times associated with other waveforms acquired at a posture similar to the posture of the patient when the current waveform was acquired.

It should be understood that while this disclosure presents examples relating to an implantable medical device for delivering fluids, aspects of this disclosure may be useful in other implantable medical devices.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described herein. These and other examples are within the scope of the following claims.

What is claimed is:

1. An implantable fluid delivery system comprising:
   a catheter;
   a fluid delivery pump coupled to the catheter, and configured to deliver a fluid through the catheter to a patient;
   at least one pressure sensor arranged to measure a pressure associated with the catheter during delivery of the fluid to the patient; and
   a processor configured to define a current pressure waveform based on the measured pressure, wherein the processor is configured to at least one of:
      determine a characteristic of the catheter based on a comparison of at least a first waveform portion of the current pressure waveform to at least a second waveform portion of a previously-acquired pressure waveform associated with the catheter during delivery of the fluid, or
      display, via a display device, at least a portion of the current pressure waveform and at least a portion of a previously-acquired pressure waveform associated with the catheter during delivery of the fluid for a user to determine a characteristic of the catheter based on a comparison of at least a portion of the current pressure waveform to at least a portion of a previously-acquired pressure waveform.

2. The system of claim 1, further comprising an implantable medical device that includes at least the fluid delivery pump, the catheter, and the at least one pressure sensor.

3. The system of claim 1, wherein the processor is further configured to determine a time for the measured pressure to fall from a maximum pressure level to a signature pressure level, wherein the signature pressure level is a pressure when a pump stroke of the implantable medical fluid delivery device is not present.

4. The system of claim 1, wherein the processor is further configured to identify one or more characteristics indicative of one or more catheter malfunctions based on the determined characteristic of the catheter.

5. The system of claim 1, wherein the processor is further configured to store at least one of: the determined characteristic of the catheter or the current pressure waveform.

6. The system of claim 1, wherein the previously-acquired pressure waveform corresponds to one or more waveforms corresponding to one or more malfunctions associated with the catheter.

7. The system of claim 1, wherein the first waveform portion of the current waveform comprises first variations in pressure over a first time, and wherein the second waveform portion of the previously-acquired waveform comprises second variations in pressure over a second time.

8. The system of claim 1, further comprising an external device that includes the processor.

9. The system of claim 8, wherein the external device further comprises a user interface configured to display the current pressure waveform associated with the measured pressure.

10. The system of claim 1, wherein the processor is configured to:
    calculate a pressure decay time based on a maximum pressure value associated with the measured pressure; and
    determine the characteristic of the catheter based on the pressure decay time.

11. The system of claim 10, wherein the decay time indicates a time required for the measured pressure to fall from the maximum pressure to a signature pressure level, wherein the signature pressure level is a pressure when a pump stroke of the implantable medical fluid delivery device is not present.

12. The system of claim 1, further comprising at least one posture sensor configured to determine a posture associated with the patient.

13. The system of claim 12, wherein the at least one posture sensor is further configured to obtain a posture associated with the patient when the at least one pressure sensor measures the pressure associated with the catheter, and wherein the processor is further configured to associate the determined characteristic of the catheter with the obtained posture.

14. The system of claim 1, wherein the processor is further configured to:
   determine whether the catheter is functioning properly; and
   cause the at least one pressure sensor to measure a current baseline pressure when the catheter is functioning properly.

15. The system of claim 14, wherein the previously-acquired pressure waveform comprises a waveform acquired when the catheter is functioning properly.

16. The system of claim 14, wherein the processor is further configured to:
   cause the at least one pressure sensor to measure a new baseline pressure; and
   determine whether to replace the current baseline pressure with the new baseline pressure.

17. A non-transitory computer-readable medium comprising instructions for causing a programmable processor in an implantable fluid delivery system to:
   deliver a fluid from the implantable medical fluid delivery device through a catheter to a patient;
   measure a pressure associated with the catheter during the delivery of the fluid to the patient;
   define a current pressure waveform based on the measured pressure; and
   at least one of:
      A) determine a characteristic of the catheter based on a comparison of at least a first waveform portion of the current pressure waveform to at least a second waveform portion of a previously-acquired pressure waveform associated with the catheter during delivery of the fluid, or
      B) display, on a display device, at least a portion of the current pressure waveform and at least a portion of a previously-acquired pressure waveform associated with the catheter during delivery of the fluid for a user to determine a characteristic of the catheter based on a comparison of at least a portion of the current pressure waveform to at least a portion of a previously-acquired pressure waveform.

18. The non-transitory computer-readable medium of claim 17, further comprising instructions for causing the programmable processor in the implantable fluid delivery system to:
   obtain a posture associated with the patient when the pressure associated with the catheter is measured; and
   associate the determined characteristic of the catheter with the obtained posture.

19. A system comprising:
   means for delivering a fluid from an implantable medical fluid delivery device through a catheter to a patient;
   means for measuring a pressure associated with the catheter during the delivery of the fluid to the patient;
   means for defining a current pressure waveform based on the measured pressure; and
   at least one of:
      (A) means for determining a characteristic of the catheter based on a comparison of at least a first waveform portion of the current pressure waveform to at least a second waveform portion of a previously-acquired pressure waveform associated with the catheter during delivery of the fluid, or
      (B) means for displaying at least a portion of the current pressure waveform and at least a portion of a previously-acquired pressure waveform associated with the catheter during delivery of the fluid for a user to determine a characteristic of the catheter based on a comparison of at least a portion of the current pressure waveform to at least a portion of a previously-acquired pressure waveform.

20. The system of claim 19, further comprising:
   means for obtaining a posture associated with the patient when the pressure associated with the catheter is measured; and
   means for associating the determined characteristic of the catheter with the obtained posture.

* * * * *